(12) United States Patent
Valle et al.

(10) Patent No.: US 11,994,519 B2
(45) Date of Patent: May 28, 2024

(54) BIOMARKERS FOR MULTIPLE SCLEROSIS

(71) Applicant: GLX Analytix ApS, København N (DK)

(72) Inventors: Brian William Della Valle, København V (DK); Casper Hempel, Dyssegård (DK); Marie Agnete Larsen, Hinnerup (DK)

(73) Assignee: GLX Analytix ApS, København (DK)

( * ) Notice: Subject to any disclaimer, the term of this patent is extended or adjusted under 35 U.S.C. 154(b) by 841 days.

(21) Appl. No.: 16/772,034

(22) PCT Filed: Dec. 13, 2018

(86) PCT No.: PCT/EP2018/084825
§ 371 (c)(1),
(2) Date: Jun. 11, 2020

(87) PCT Pub. No.: WO2019/115724
PCT Pub. Date: Jun. 20, 2019

(65) Prior Publication Data
US 2021/0215691 A1   Jul. 15, 2021

(30) Foreign Application Priority Data

Dec. 13, 2017 (EP) .................... 17207028

(51) Int. Cl.
*B01L 3/00* (2006.01)
*B01F 23/00* (2022.01)
(Continued)

(52) U.S. Cl.
CPC .............. *G01N 33/564* (2013.01); *C08L 5/08* (2013.01); *G01N 2400/40* (2013.01); *G01N 2800/285* (2013.01)

(58) Field of Classification Search
CPC ......... G01N 33/6896; G01N 33/54306; G01N 33/54313; G01N 2333/435; G01N 2560/00; G01N 33/6848
See application file for complete search history.

(56) References Cited

U.S. PATENT DOCUMENTS

2007/0231319 A1 * 10/2007 Yednock ................. A61P 31/18
424/131.1
2010/0203569 A1 * 8/2010 Dotan ................ G01N 33/6896
435/29
(Continued)

FOREIGN PATENT DOCUMENTS

WO   WO-2016032349 A1 *   3/2016   ....... G01N 33/57407

OTHER PUBLICATIONS

Miller, D. H., F. Barkhof, and J. J. P. Nauta. "Gadolinium enhancement increases the sensitivity of MRI in detecting disease activity in multiple sclerosis." Brain 116.5 (1993): 1077-1094. (Year: 1993).*
(Continued)

*Primary Examiner* — Jennifer Wecker
*Assistant Examiner* — Oyeleye Alexander Alabi
(74) *Attorney, Agent, or Firm* — Knobbe Martens Olson & Bear LLP

(57) ABSTRACT

The present invention relates to biomarkers associated with multiple sclerosis (MS), particular GLX molecules, and teven more particular GLX-related glycosaminoglycans (GAGs) and GLX-related proteoglycans (PGs).

29 Claims, 14 Drawing Sheets

(51) Int. Cl.

| | | |
|---|---|---|
| B01F 23/41 | (2022.01) | |
| B01F 101/23 | (2022.01) | |
| B23Q 17/24 | (2006.01) | |
| C08L 5/08 | (2006.01) | |
| C12M 1/34 | (2006.01) | |
| C12Q 1/04 | (2006.01) | |
| C12Q 1/18 | (2006.01) | |
| G01N 21/3577 | (2014.01) | |
| G01N 21/359 | (2014.01) | |
| G01N 21/39 | (2006.01) | |
| G01N 21/45 | (2006.01) | |
| G01N 21/64 | (2006.01) | |
| G01N 30/12 | (2006.01) | |
| G01N 30/68 | (2006.01) | |
| G01N 30/70 | (2006.01) | |
| G01N 30/72 | (2006.01) | |
| G01N 30/88 | (2006.01) | |
| G01N 33/00 | (2006.01) | |
| G01N 33/18 | (2006.01) | |
| G01N 33/50 | (2006.01) | |
| G01N 33/564 | (2006.01) | |
| G01N 33/68 | (2006.01) | |

(56) References Cited

U.S. PATENT DOCUMENTS

| | | | | |
|---|---|---|---|---|
| 2010/0304424 | A1* | 12/2010 | Vink | A61P 29/00 |
| | | | | 435/29 |
| 2011/0045514 | A1* | 2/2011 | Muntendam | G01N 33/6893 |
| | | | | 435/15 |
| 2012/0040383 | A1* | 2/2012 | Jia | G01N 33/57423 |
| | | | | 422/68.1 |
| 2012/0045781 | A1* | 2/2012 | Veidal | C12Q 1/37 |
| | | | | 435/7.1 |
| 2016/0187343 | A1* | 6/2016 | Franzmann | G01N 33/6827 |
| | | | | 702/179 |
| 2018/0328939 | A1* | 11/2018 | Alonso Sampedro | |
| | | | | G01N 33/6839 |
| 2019/0086416 | A1* | 3/2019 | Daaboul | G01N 21/253 |

OTHER PUBLICATIONS

Borody, Thomas, et al. "Fecal microbiota transplantation (FMT) in multiple sclerosis (MS): 942." Official journal of the American College of Gastroenterology| ACG 106 (2011): S352. (Year: 2011).*

Baranzini, Sergio E. et al., "Genome-wide association analysis of susceptibility and clinical phenotype in multiple sclerosis" Human Molecular Genetics, 2009, pp. 767-778, vol. 18, No. 4.

Coulson-Thomas, Yvette M. et al., "The Identification of Proteoglycans and Glycosaminoglycans in Archaeological Human Bones and Teeth" PLOS ONE, Jun. 2015, pp. 1-21, vol. 10, No. 6.

Halimi, Michele et al., "Prion urine comprises a glycosaminoglycan-light chain IgG complex that can be stained by Congo red" Journal of Virological Methods, 2006, pp. 205-210, vol. 133.

Kurup, Ravi Kumar et al., "Hypothalamic Digoxin and Hypomagnesemia in Relation to the Pathogenesis of Multiple Sclerosis" The Journal of Trace Elements in Experimental Medicine, 2002, pp. 211-220, vol. 15.

Raphael, Itay et al., "Body fluid biomarkers in multiple sclerosis: how far we have come and how they could affect the clinic now and in the future" Expert Rev Clin Immunol., Jan. 2015, pp. 69-91, vol. 11, No. 1.

International Search Report for PCT/EP2018/084825 dated May 29, 2019.

* cited by examiner

A
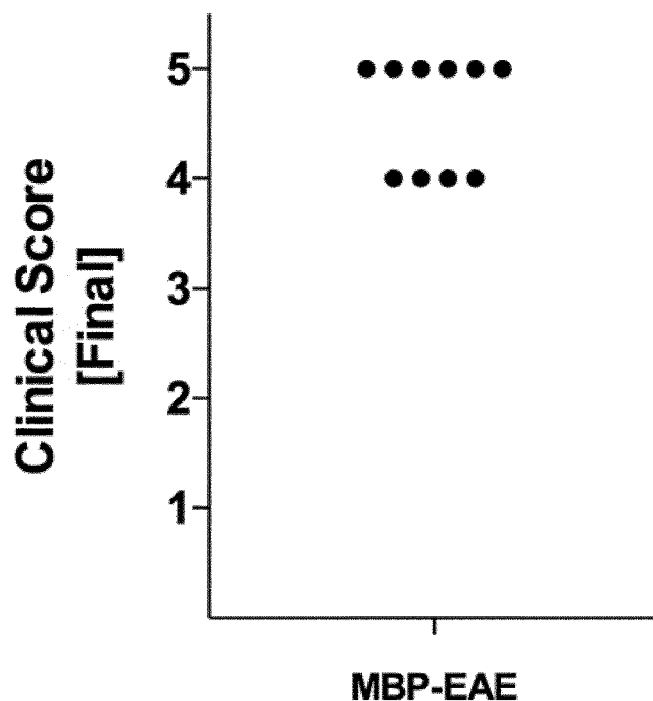
B
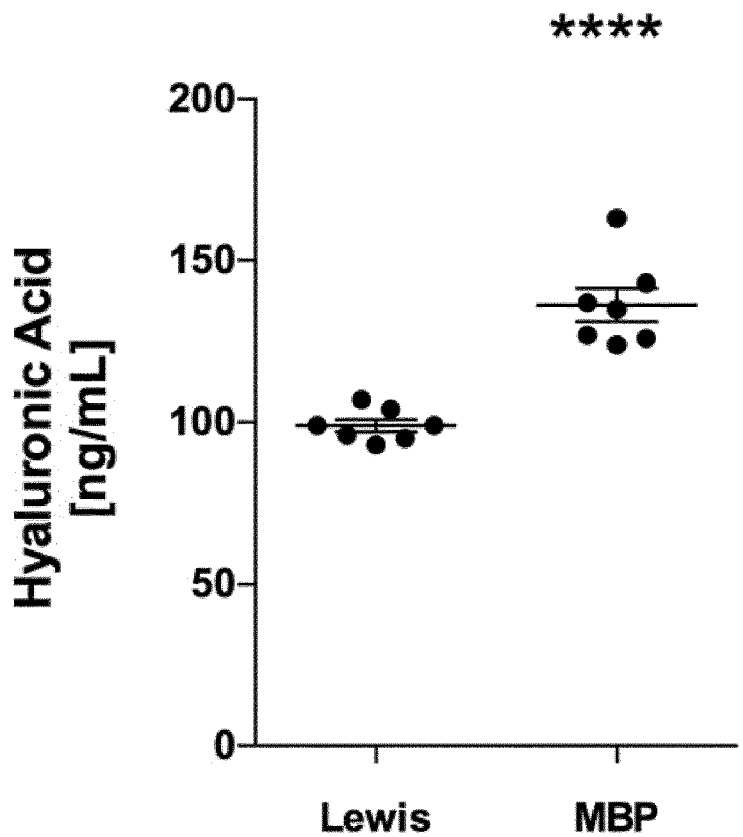
Fig. 1, continues

C
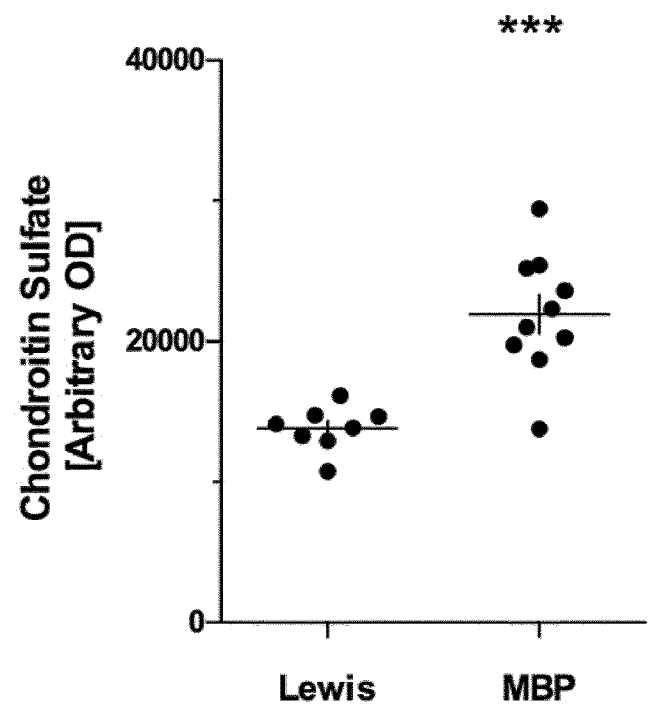
D
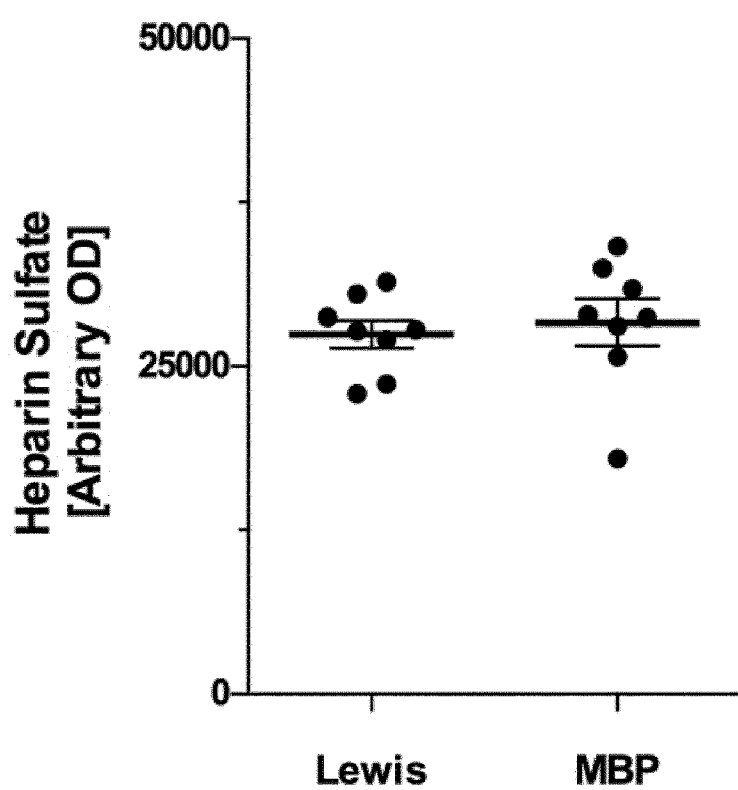
Fig. 1, continues

E
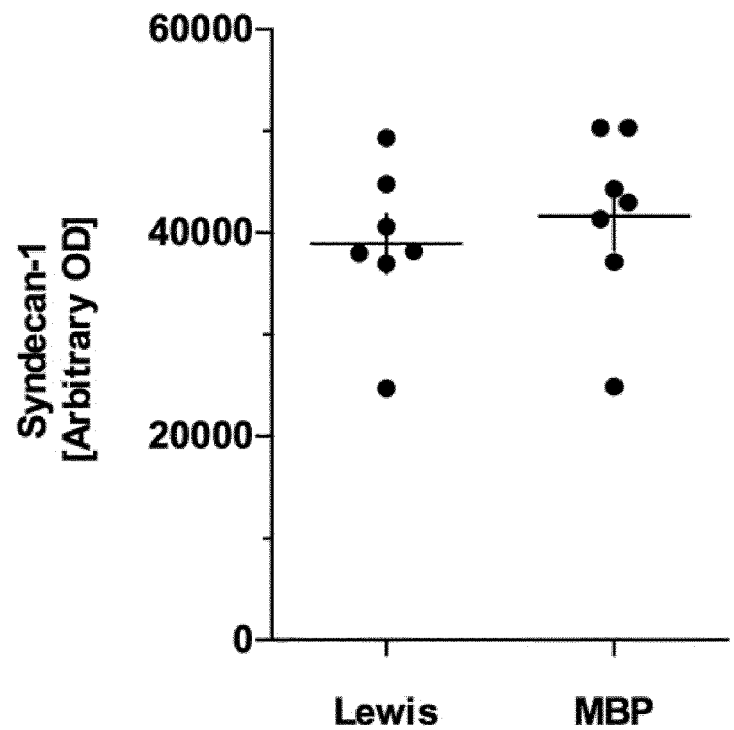
F
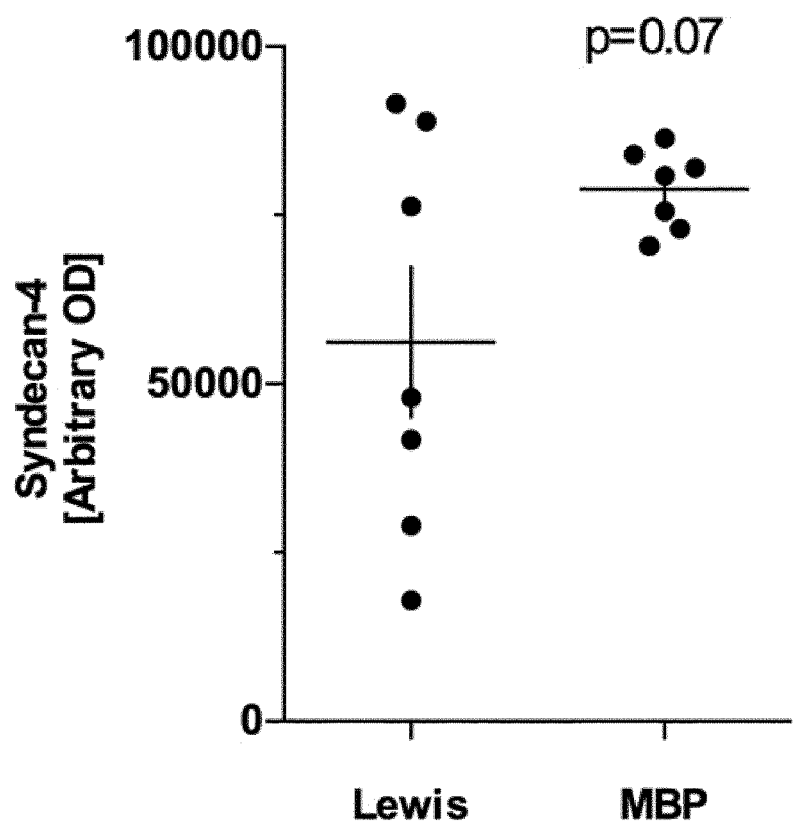
Fig. 1, continued

A
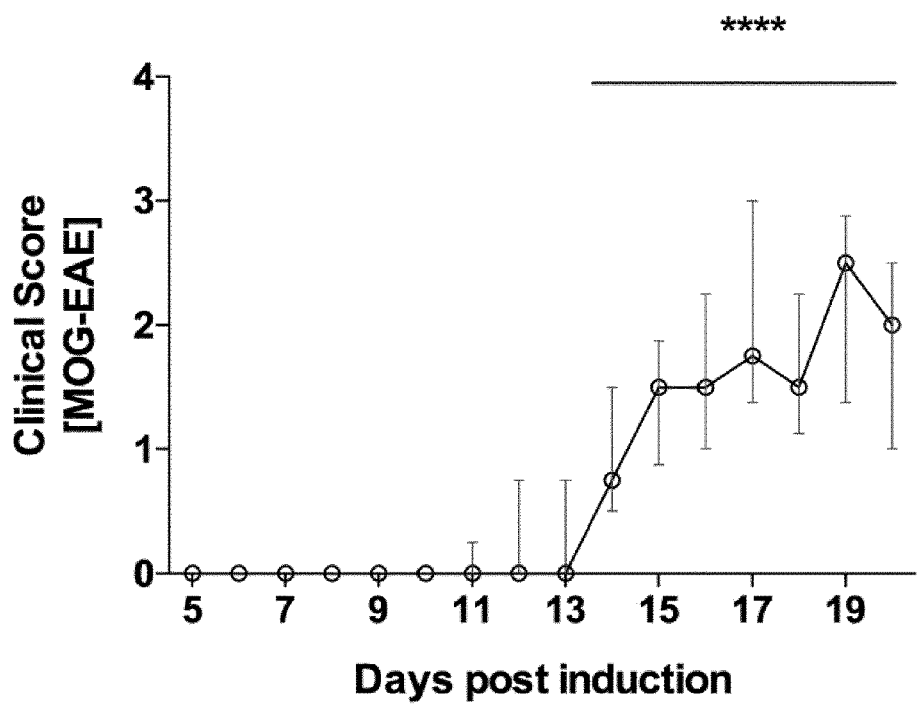
B
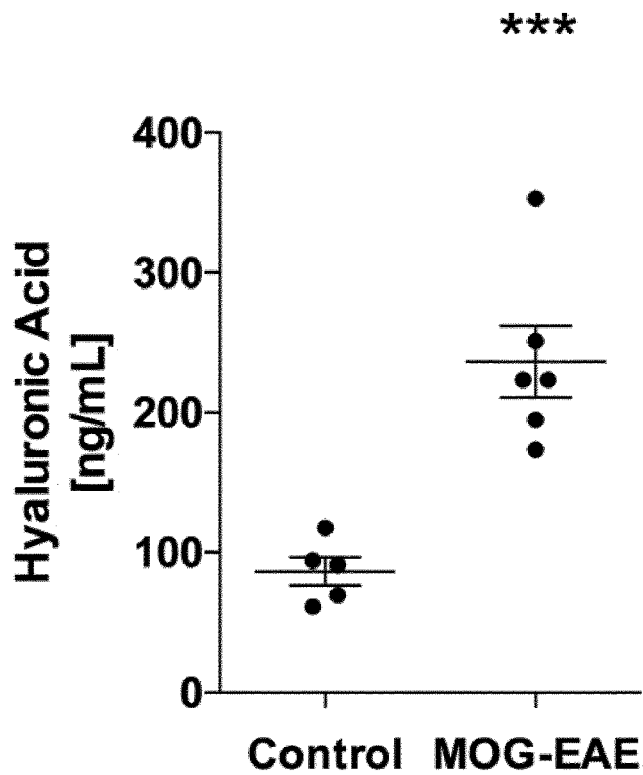
Fig. 2. continues

C
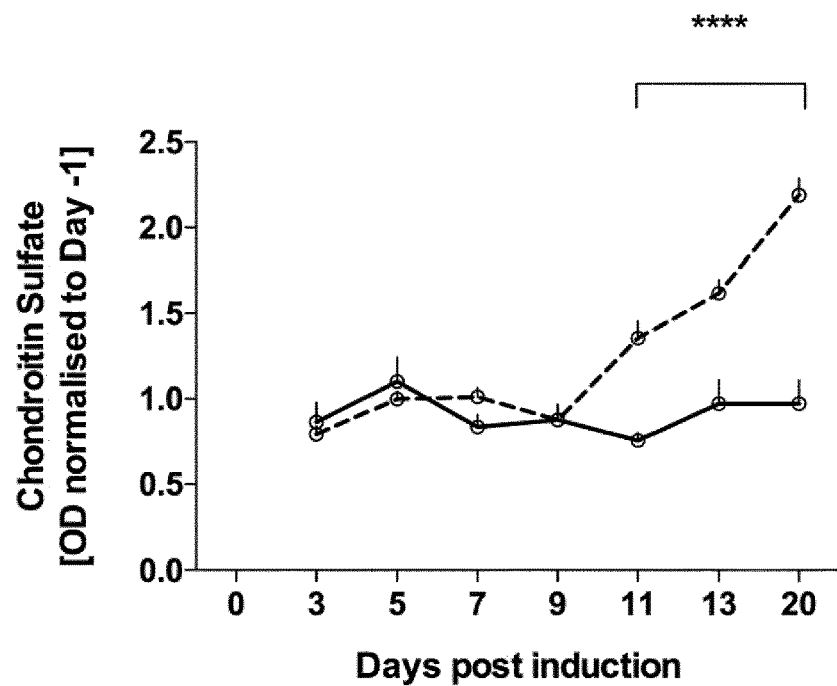
D
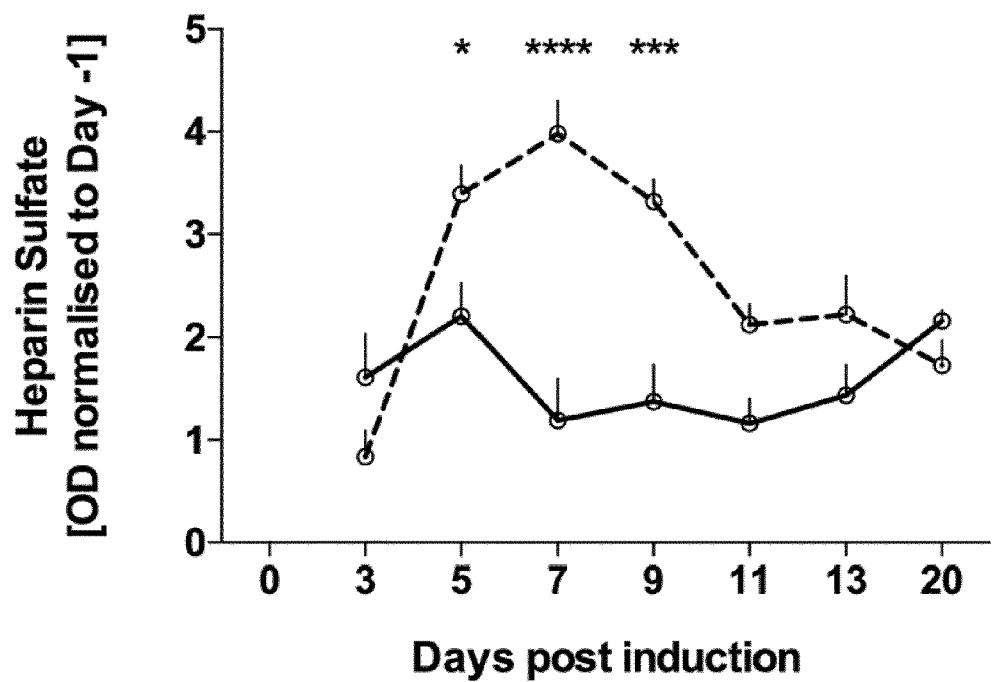
Fig. 2. continues

E

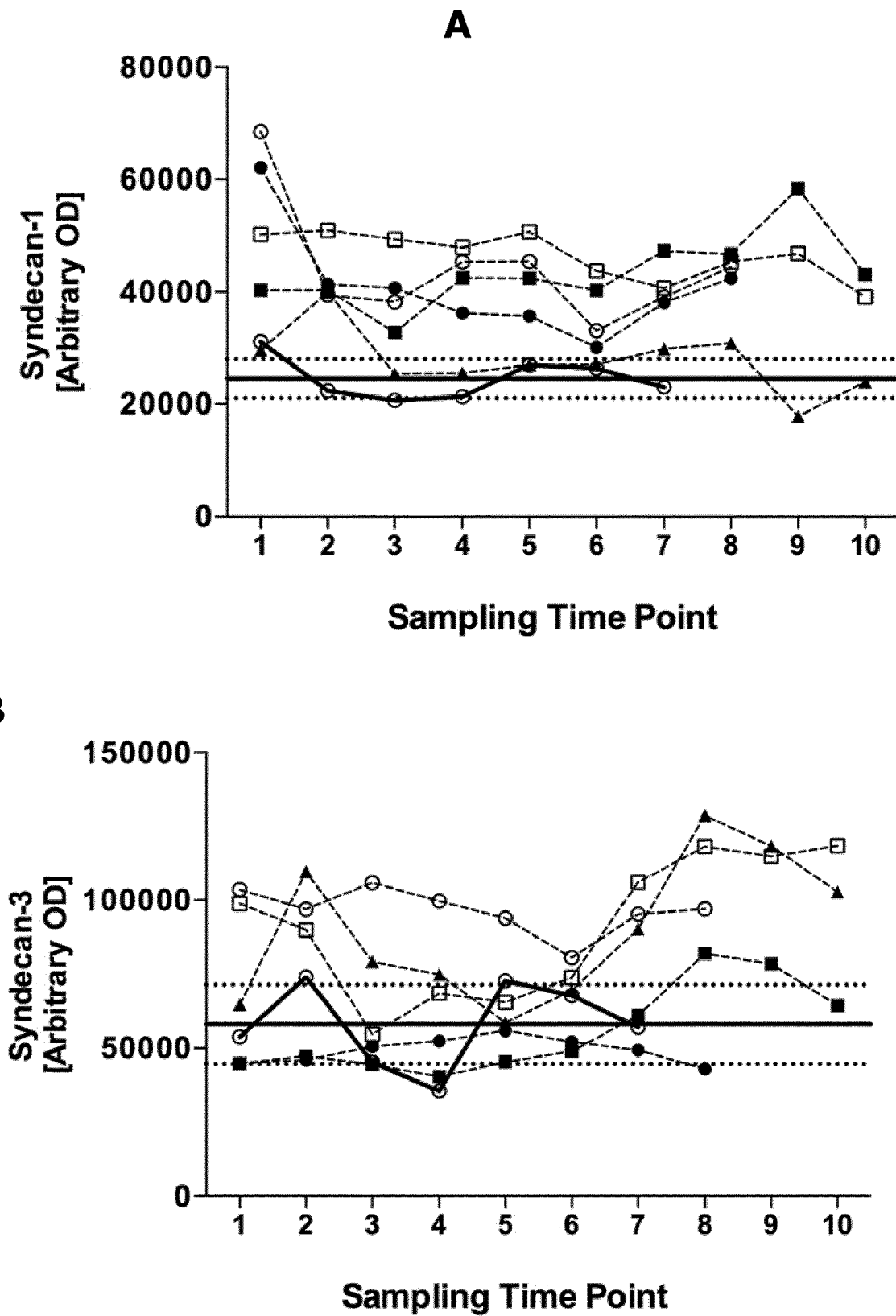
Fig. 3. continues

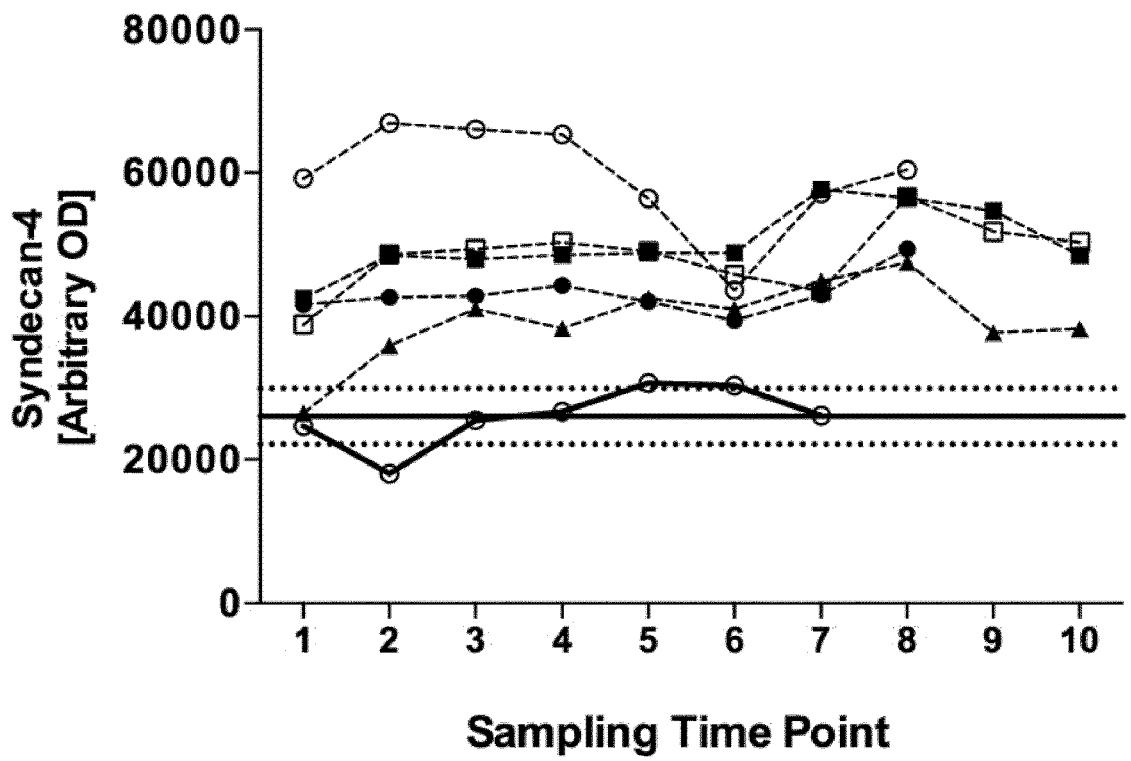
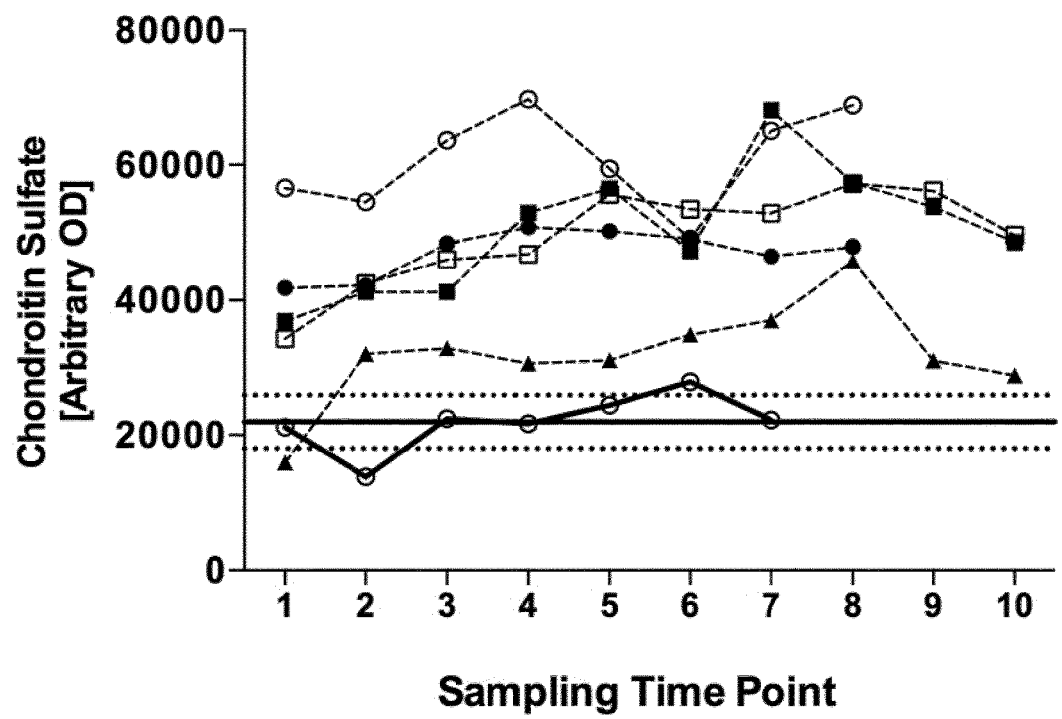
Fig. 3. continues

E
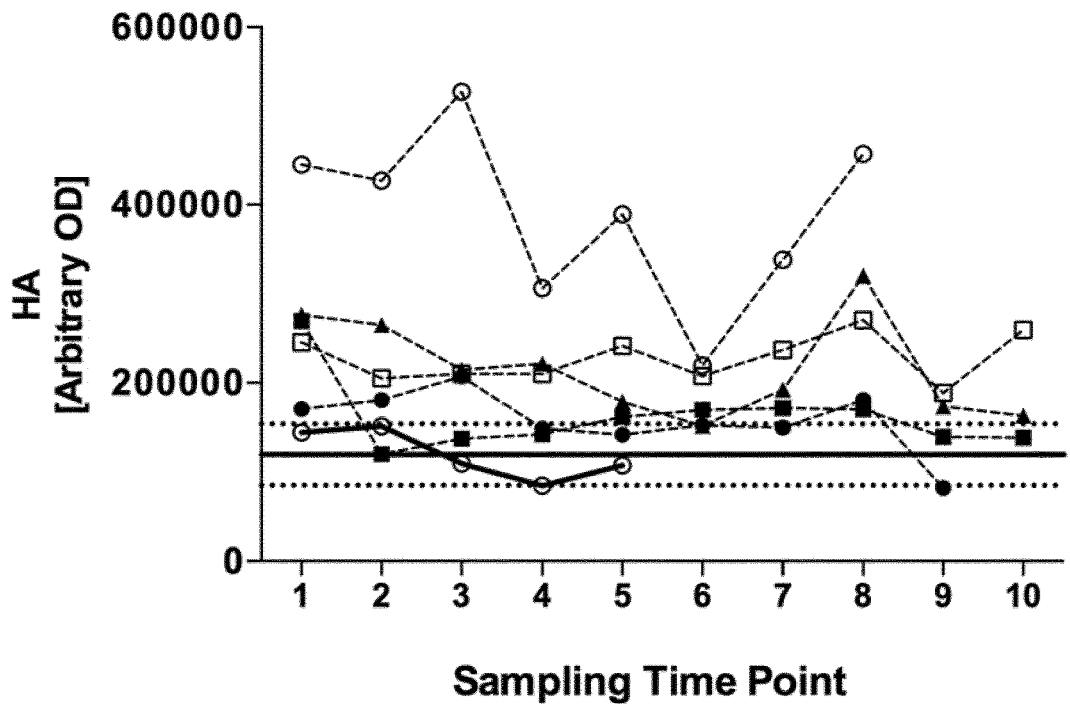
F
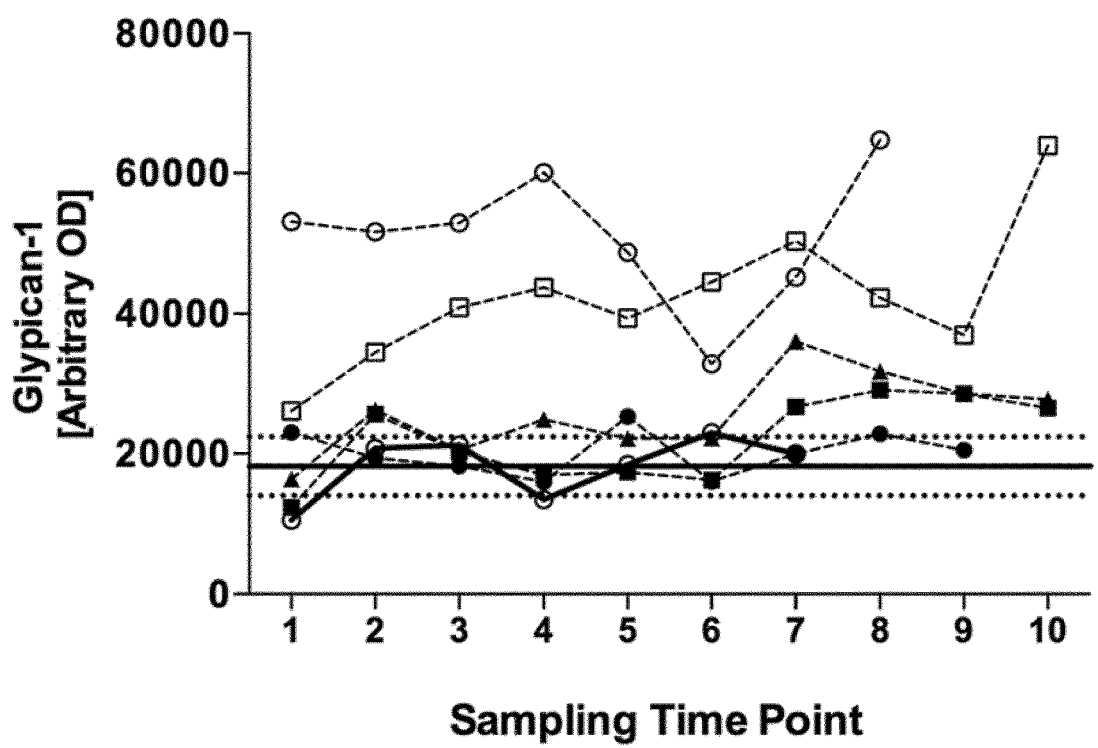
Fig. 3. Continues

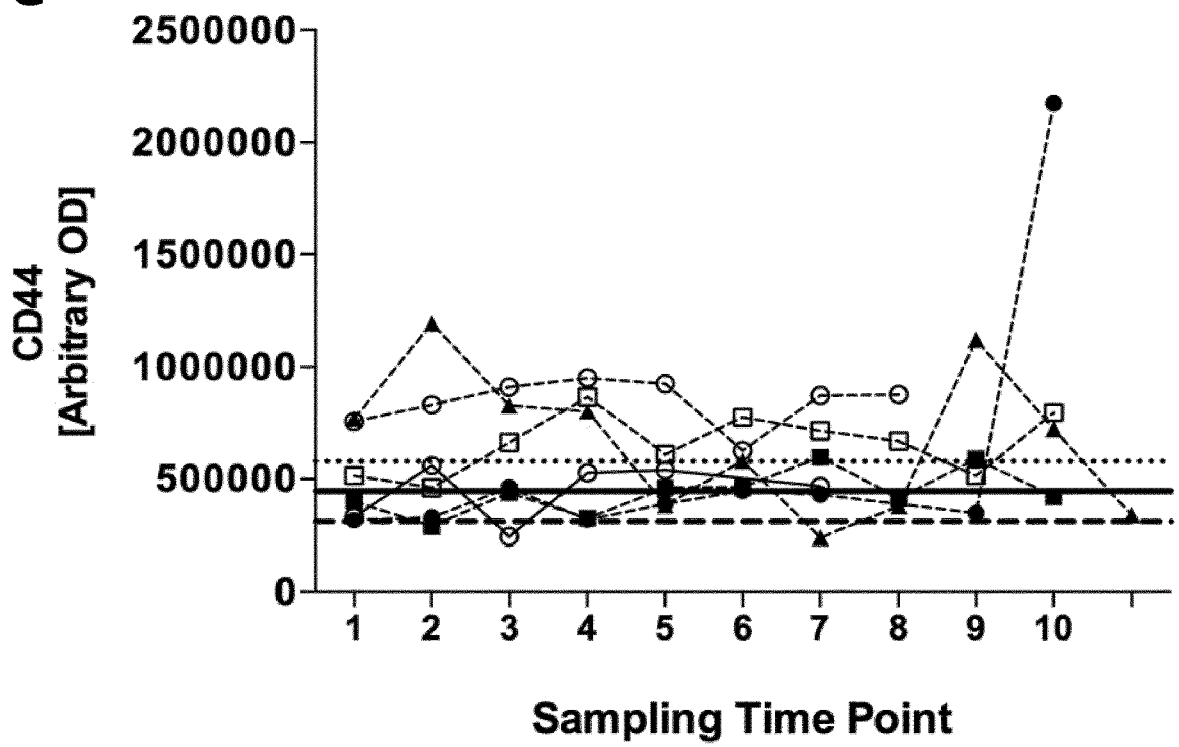
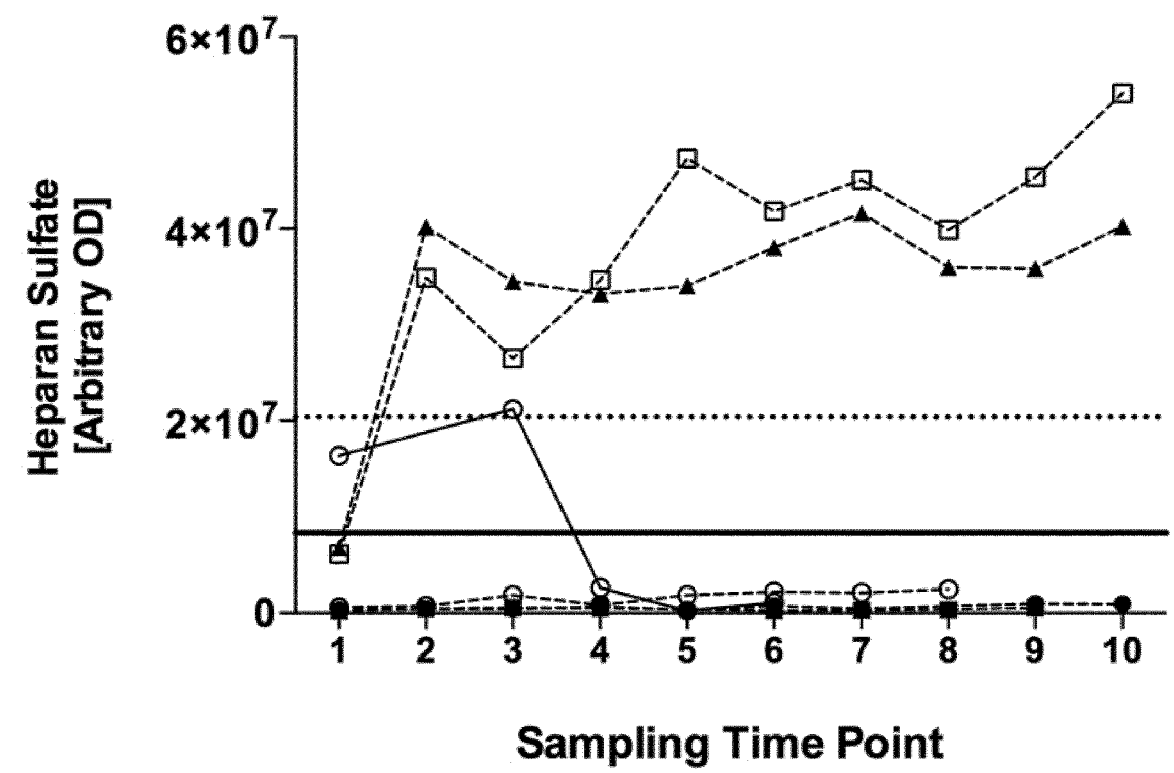
Fig. 3. Continued

A
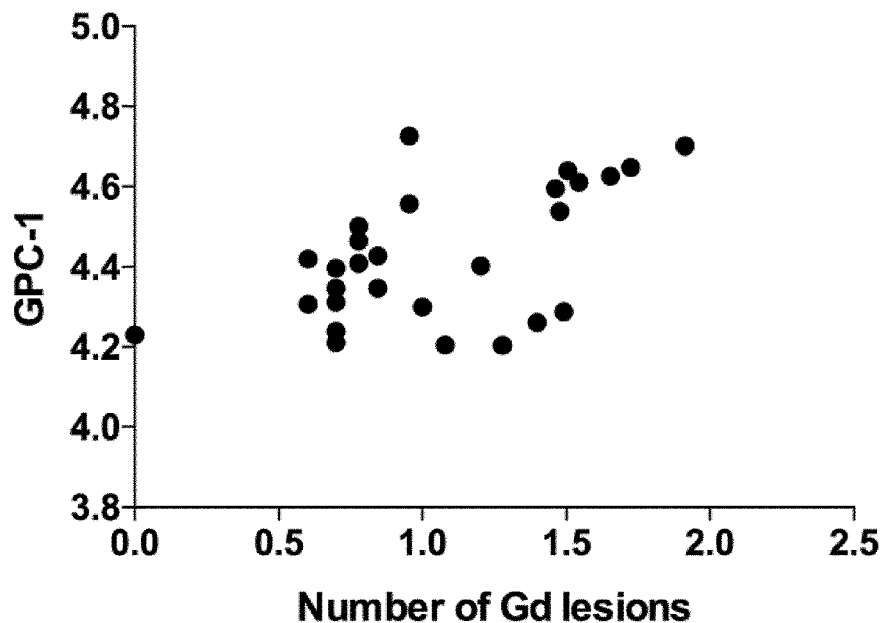
B
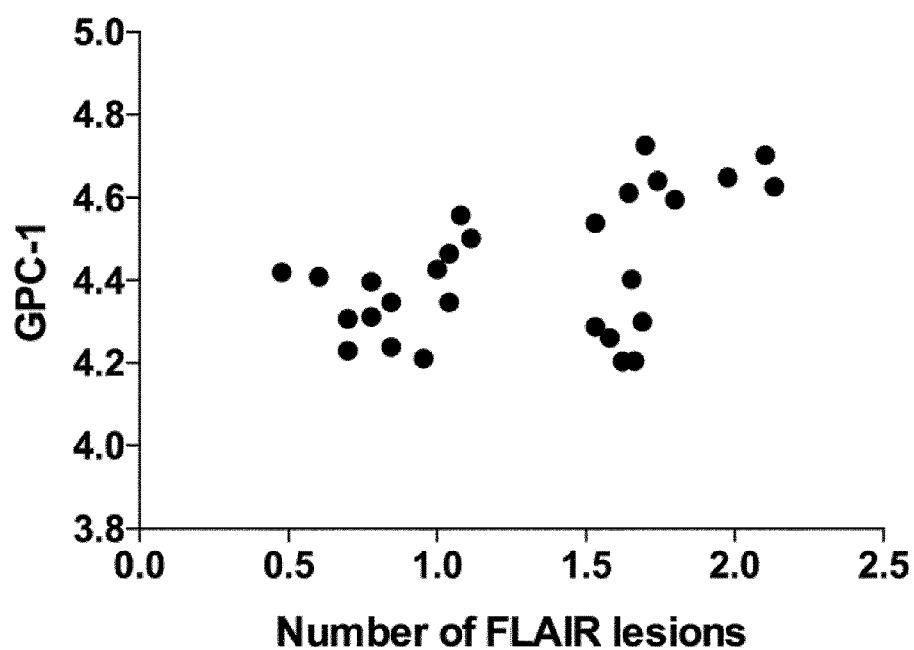
Fig. 4. Continues

C
0.42
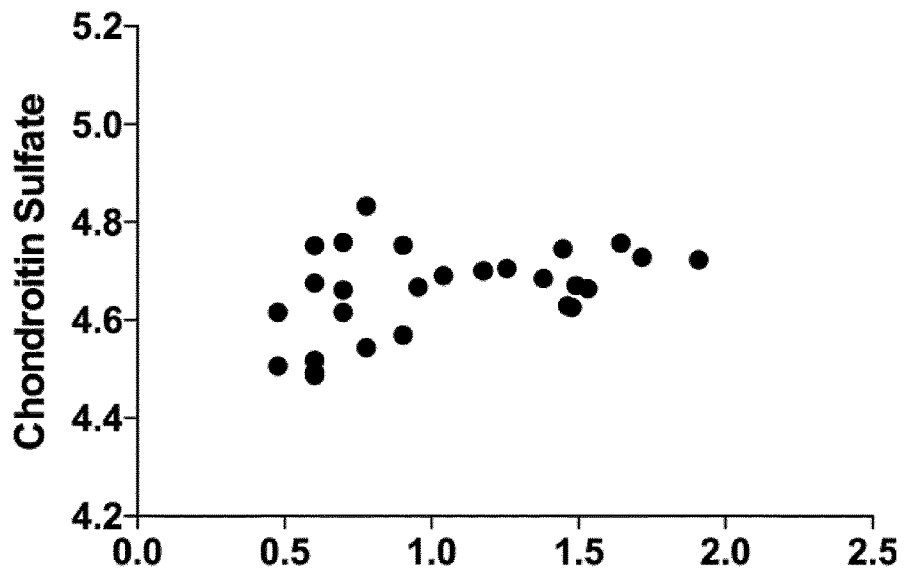
D
0.51
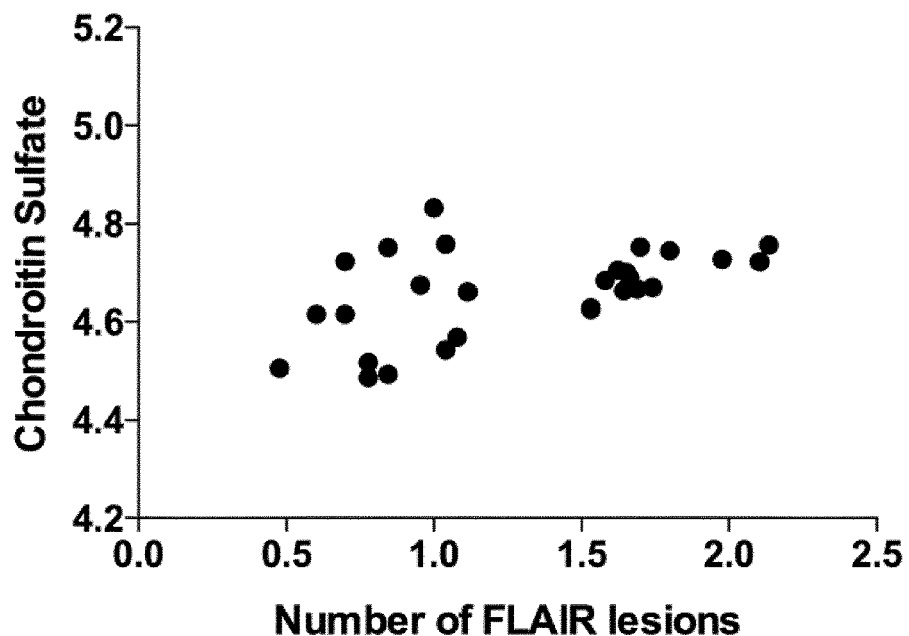
Fig. 4. Continues

E
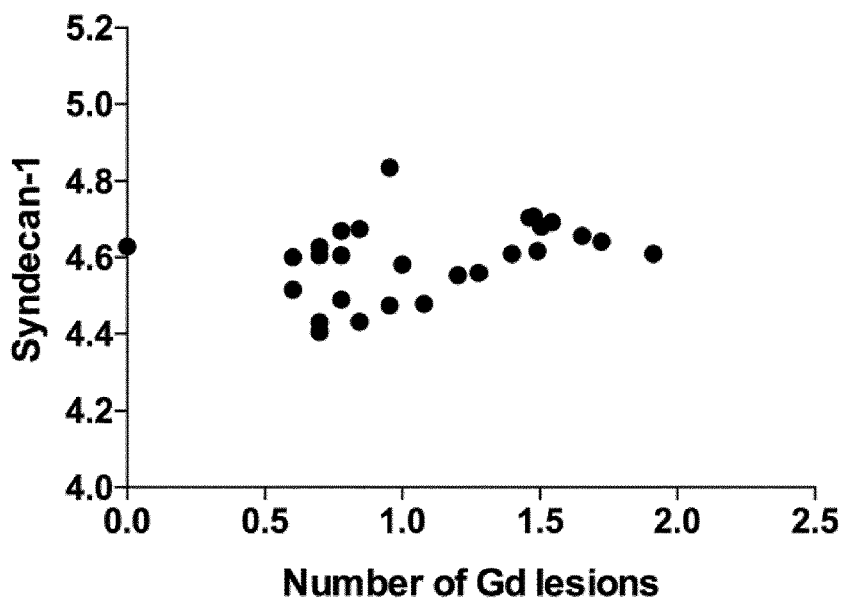
F
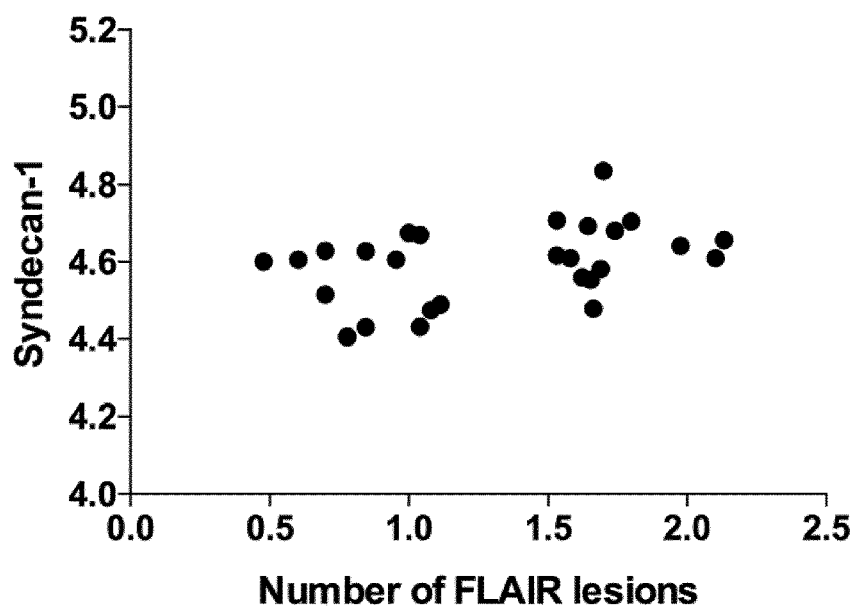
Fig. 4. Continued

BIOMARKERS FOR MULTIPLE SCLEROSIS

CROSS REFERENCE TO RELATED APPLICATIONS

This application is a U.S. National Phase Application of PCT International Application Number PCT/EP2018/084825, filed on Dec. 13, 2018, designating the United States of America and published in the English language, which is an International Application of and claims the benefit of priority to European Patent Application No. 17207028.6, filed on Dec. 13, 2017. The disclosures of the above-referenced applications are hereby expressly incorporated by reference in their entireties.

TECHNICAL FIELD OF THE INVENTION

The present invention relates to biomarkers for the prediction of the risk of developing and/or having multiple sclerosis (MS). The invention also relates to staging/subtyping MS. Further, the invention relates to methods for evaluating treatment protocols for MS and for assisting in the prognosis of MS.

BACKGROUND OF THE INVENTION

Multiple sclerosis (MS) is a devastating autoimmune disease, often afflicting those in the prime of their lives. Despite high patient-to-patient variability, general classifications of the disease course can be discerned based on the disease presentation and progression. These classifications are associated with variable outcomes and treatment responses. Current MS treatments are non-curative, side-effect prone, and expensive, highlighting the need for expanded treatment options for patients. Moreover, despite the advent of proteomics for assessing biomarkers, there is a need for new biomarkers for disease severity, predicting future attacks and treatment response.

Current gold-standard diagnosis involves MRI scanning for numbers of lesions and lesion size, and disease symptoms. In some cases, oligoclonal bands are assessed in patient cerebrospinal fluid.

Thus, there is an unmet medical need in the biomedical research field of multiple sclerosis. Presently, diagnostic tools, including biomarkers—ideally obtained in a minimally-invasive manner—for disease diagnosis, prognosis and treatment-response are lacking.

Hence, an improved method to predict the risk of developing multiple sclerosis would be advantageous.

SUMMARY OF THE INVENTION

The present invention relates to the identification of biomarkers associated with Multiple sclerosis (MS), particular glycocalyx (GLX) molecules, and even more particular GLX-related glycosaminoglycans (GAGs) and GLX-related proteoglycans (PGs). Heparan sulfate, chondroitin sulfate, dermatan sulfate, keratan sulfate and hyaluronic acid are GAGs shed from the GLX earlier than their membrane-anchored PG ectodomains and thus represent an early stage biomarker for attack or severity. In the present study, two variations of a well-described rodent model of MS (experimental autoimmune encephalitis (EAE)) was initially used to identify new potential biomarkers associated with disease debut and progression (example 1). These data suggested GLX-related Glycosaminoglycans (GAGs) and GLX-related Proteoglycans (PGs) as biomarker for the presence of MS and/or attack or severity in MS. These results were then further validated in blood samples from human subjects suffering from MS (Example 2).

Thus, the present invention relates to glycocalyx (GLX) molecules, as early stage predictors of immune attack, BBB breakdown, disease severity, and treatment efficacy, especially in relation to multiple sclerosis (MS). Thus, an object of the present invention relates to the provision of novel biomarkers for MS. In particular, it is an object of the present invention to provide biomarkers that solves the above-mentioned problems of the prior art with early prediction.

Thus, one aspect of the invention relates to a method for determining the risk of having or developing multiple sclerosis, in a subject, the method comprising
  providing a biological sample from a subject;
  determining the level of at least one biomarker selected from the group consisting of GLX-related glycosaminoglycans (GAGs) and GLX-related proteoglycans (PGs) in said biological sample;
  comparing said levels of one or more biomarkers to one or more corresponding reference levels; and
  determining that said subject is at risk of developing and/or having multiple sclerosis, if said level of one or more biomarkers are above the one or more reference levels, or determining that said subject is not at risk of developing or having multiple sclerosis, if said one or more levels are equal to or below the one or more reference levels.

In a preferred embodiment, the biomarkers are selected from the group consisting of Glycosaminoglycans:
  Chondroitin Sulfates (CS);
  Hyaluronic Acids (HA);
  Heparan Sulfates (HS)
  Dermatan Sulfates (DS)
  Keratan Sulfates (KS)
  Proteoglycans:
  Syndecan-1;
  Syndecan-2
  Syndecan-3;
  Syndecan-4; and
  Glypican-1;
  Glypican-2
  Glypican-3
  Glypican-4
  Glypican-5
  Glypican-6
  BiGlycan
  Perlecan
  Mimecan
  Decorin
  Versican In yet a preferred embodiment, the method also comprises subgrouping/staging the disease and/or providing a prognosis for said subject.

Another aspect of the present invention, relates to a method for evaluating the efficacy of a treatment protocol for prevention, treatment, delay and/or alleviation of multiple sclerosis, the method comprising
  completing the method according to the invention; and
  for a subject considered at risk of having or developing multiple sclerosis, evaluating whether a treatment protocol for the prevention, treatment, delay or alleviation of multiple sclerosis, results in that said subject is not developing multiple sclerosis, is treated for multiple sclerosis, has delayed disease progression or is alleviated.

Yet another aspect of the present invention, is to provide a method for monitoring disease progression or regression of multiple sclerosis in a subject, the method comprising
  providing a first biological sample from a subject considered as having multiple sclerosis or at risk of developing multiple sclerosis;
  determining the level of at least one biomarker selected from the group consisting of GLX-related glycosaminoglycans (GAGs) and GLX-related proteoglycans (PGs), in said first biological sample;
  providing a second biological sample from the subject, wherein said second sample has been obtained at a later time point than said first sample from said subject;
  determining the level of at least one biomarker selected from the group consisting of GLX-related glycosaminoglycans (GAGs) and GLX-related proteoglycans (PGs), in said second biological sample;
  comparing said levels of one or more biomarkers in said second sample to said one or more corresponding levels in the first sample; and
  determining that
    said subject has a regression of the multiple sclerosis, if said level of one or more biomarkers in the second sample are lower than the levels in said first sample, or
    determining that said subject has a progression of the multiple sclerosis, if said level of one or more biomarkers in the second sample are higher than the levels in said first sample, or
    determining that said subject has no regression or progression of the multiple sclerosis, if said level of one or more biomarkers in the second sample are equal to the levels in said first sample.

A further aspect relates to a method for evaluating the efficacy of treatment to prevent, treat, delay or alleviate multiple sclerosis in a subject, the method comprising
  providing a first biological sample from a subject;
  determining the level of at least one biomarker selected from the group consisting of GLX-related glycosaminoglycans (GAGs) and GLX-related proteoglycans (PGs);
  providing a second biological sample from the subject, wherein said second sample has been obtained at a later time point than said first sample from said subject, and wherein a treatment regime against MS has been initiated or completed between the sampling of the first sample and sampling of the second sample;
  determining the level of at least one biomarker selected from the group consisting of GLX-related glycosaminoglycans (GAGs) and GLX-related proteoglycans (PGs), in said second biological sample;
  comparing said levels of one or more biomarkers in said second sample to said one or more corresponding levels in the first sample; and
  determining that said treatment protocol is working against MS in said subject, if said level of one or more biomarkers in the second sample are lower than or equal to the levels in said first sample, or determining that said treatment protocol is NOT working against MS in said subject if said level of one or more biomarkers in the second sample are higher than the levels in said first sample.

Yet an aspect of the invention relates to a kit comprising binding agents for at least two biomarkers selected from the group consisting of GLX-related glycosaminoglycans (GAGs) and GLX-related proteoglycans (PGs); and Optionally, instructions for using said binding agent in the evaluation of multiple sclerosis in a subject.

BRIEF DESCRIPTION OF THE FIGURES

FIG. 1

Figure 2:
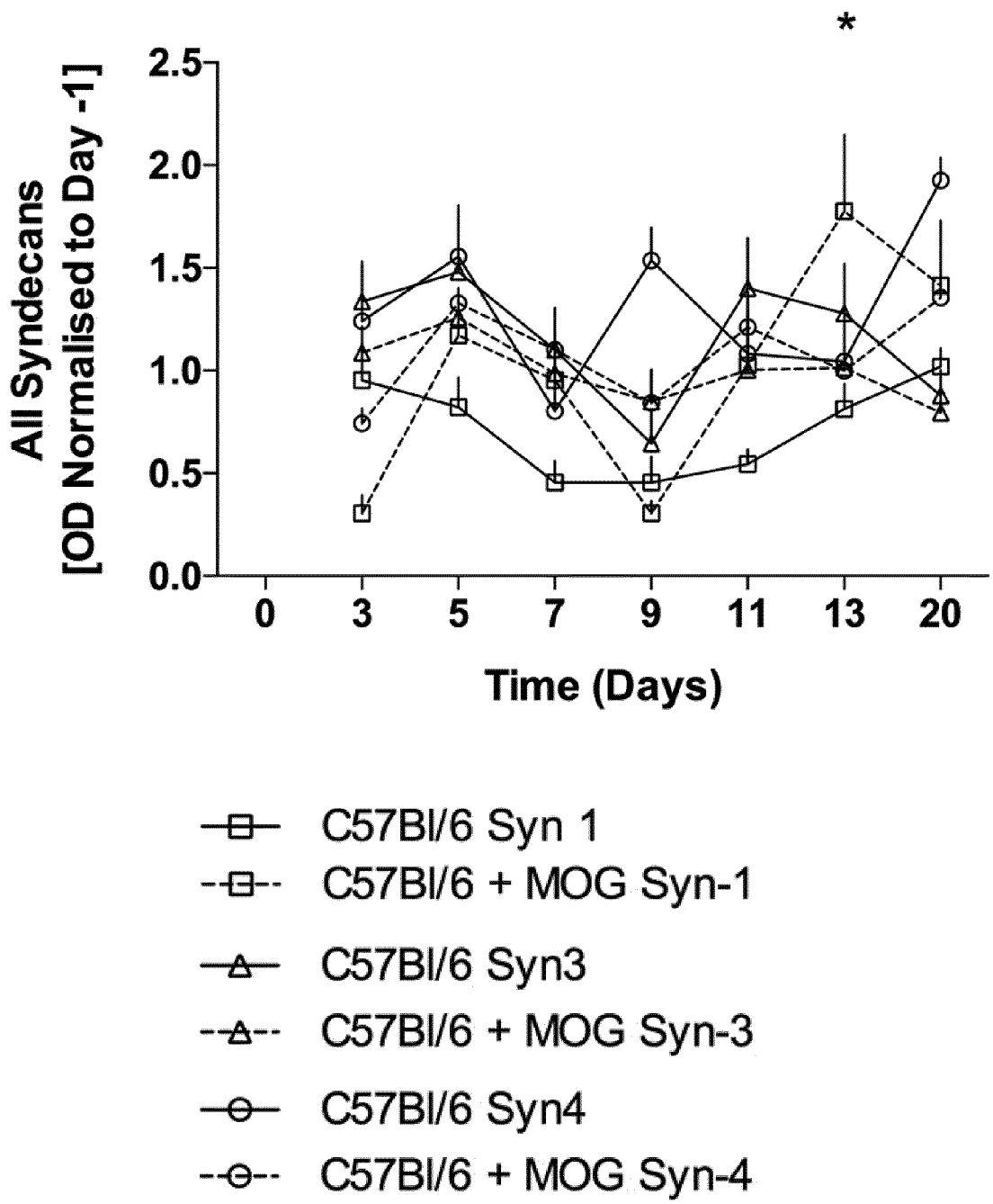

Sugar-based glycocalyx (GLX) markers are increased in late-stage of experimental MS in Lewis rats (MBP-EAE). A) Clinical scoring at late-stage of disease progressive (5 is maximum scoring). B) Sugar-based GLX marker hyaluronic acid (HA) is significantly increased in rat plasma at the peak stage of disease (ELISA). C) Chondroitin sulfate (CS) is also significantly increased in plasma at peak stage of disease. D) Heparan Sulfate is not different at peak disease. E) Syndecan-1. F) Syndecan-4. Proteoglycan markers, syndecan-1 and 4, are largely variable and unchanged at peak disease. *, , *, **** $p<0.05, 0.01, 0.001, 0.0001$.

FIG. 2

Glycocalyx (GLX) markers follow disease course in murine experimental MS (EAE). A) Clinical scoring displays classical EAE progressive paralysis until peak disease (termination of study). B) Sugar-based GLX marker hyaluronic acid (HA) is significantly increased at the peak stage of disease (ELISA). C) Chondroitin sulfate (CS) rising in the plasma of EAE mice ~2 days before symptoms manifest and continues to rise as the disease worsens. [Solid line=Control mice; Dotted line=EAE mice] D) Heparan Sulfate rises in the plasma of EAE mice at an early phase, before disease symptom debut [Solid line=Control mice; Dotted line=EAE mice]. E) Proteoglycan markers, syndecans, are largely variable and unchanged up to peak disease. *, , *, **** $p<0.05, 0.01, 0.001, 0.0001$.

FIG. 3

Glycocalyx (GLX) markers are substantially increased in the blood of five multiple sclerosis (MS) patients, relative to healthy controls. All graphs plot five patients whom were followed for 8 to 10 weeks (weekly sampling) against seven healthy controls. Closed black line represents healthy control mean and dotted lines represent the two 95% confidence intervals of healthy control samples. Patient samples are split lines with the following symbols: closed circle=Patient 1; open circle=Patient 2; closed square=Patient 3; open square=Patient 4; closed triangle=Patient 5.

A) Syndecan-1 is increased in MS patient blood for all patients except patient 5; B) Syndecan-3 is variable over time in all patients and is significantly increased in patient 2 and 5;
C) Syndecan-4 is increased in all patient blood at all time points (exception: time point 1, patient 5);
D) Sugar-based chondroitin sulfate (CS) is significantly increased in all patients at all time points (exception: time point 1, patient 5);
E) Sugar-based hyaluronic acid (HA) is significantly increased in three of five patients across all time points;
F) Proteoglycan glypican-1 is significantly increased in two patients across all time points.

Syndecan-4 and chondroitin sulfate (CS) have markedly similar curves for each patient and are consistent in their ability to predict diseased versus non-diseased regardless of time point. Patient 2 is significantly increased across all GLX markers, and patient 4 is also consistently elevated in most GLX markers.

G) Proteoglycan CD44 is increased in patients across most time points, and
H) Glycosaminoglycan Heparan Sulfate is substantially increased in two patients and not increased in three.

FIG. 4

Glycocalyx (GLX) markers are correlated to brain lesions, as measured by gadolinium (GD)-enhanced and fluid attenuation inversion recovery (FLAIR). Gd and FLAIR lesions were measured and plotted against the respective GLX measurements for the same time point. GLX markers with a correlation co-efficient above 0.4 and statistically significant (p<0.05), were included (log-transformation to normalize, thereafter Pearson correlation analysis). Glypican-1, Chondroitin Sulfate, and Syndecan-1 showed correlations with lesion changes in the brain.

FIG. 5

Proteoglycan, BiGlycan (BG), a component of the glycocalyx, is increased in blood of multiple sclerosis patients and proteoglycan Syndecan-3 is present in cerebrospinal fluid in multiple sclerosis albeit at lower levels than plasma. Blood from nineteen multiple sclerosis patients and twenty healthy controls was tested for BiGlycan in the dot blot method described. BG is significantly higher in MS patients than in healthy controls. Cerebrospinal fluid (CSF) and plasma levels of syndecan-3 were tested in nine MS patients. Syndecan-3 was present in the CSF of MS patients albeit to a lower level than plasma. Data in a, b are normal and statistics are derived from Student's T-test (p<0.01, *p<0.001)

The present invention will now be described in more detail in the following.

DETAILED DESCRIPTION OF THE INVENTION

Definitions

Prior to discussing the present invention in further details, the following terms and conventions will first be defined:

Multiple Sclerosis

Multiple sclerosis (MS) is a demyelinating disease in which the insulating covers of nerve cells in the brain and spinal cord are damaged. Subtypes of MS are Clinically isolated syndrome (CIS), Relapsing-remitting MS (RRMS), Primary progressive MS (PPMS) and Secondary progressive MS (SPMS).

GLX Molecules

The "GLX" or "glycocalyx" is the carbohydrate-rich outer part of the cell surface of the majority of cells in the body, including the luminal endothelium. This layer is the first interaction between the blood and the vessel wall, both throughout the body and at the blood-brain barrier (BBB) junction. As described in here, shedding of the GLX may be an early stage predictor of MS, disease severity of MS, and treatment efficacy of MS. Examples of GLX molecules are Glycosaminoglycans (GAGs) and Proteoglycans (PGs). These may be brain derived.

Thus, the term "GLX-related" is to be understood as molecules associated with (or has been associated with) the GLX structure. Phrased in another way, the "GLX-related" may be understood as molecules originating from the GLX structure.

Glycosaminoglycan (GAG's)

Glycosaminoglycan (GAGs) or "mucopolysaccharides" are long unbranched polysaccharides consisting of a repeating disaccharide unit. The repeating unit (except for keratan) consists of an amino sugar (N-acetylglucosamine or N-acetylgalactosamine) along with an uronic sugar (glucuronic acid or iduronic acid) or galactose. Examples of Glycosaminoglycan (GAGs) forming part of the present invention are:

Chondroitin sulfate: Chondroitin sulfate (CS) is a sulfated glycosaminoglycan (GAG) composed of a chain of alternating sugars (N-acetylgalactosamine and glucuronic acid). It is usually found attached to proteins as part of a proteoglycan.

Hyaluronic acid: Hyaluronic acid (HA) also called hyaluronan, is an anionic, nonsulfated glycosaminoglycan (GAG) distributed widely throughout connective, epithelial, and neural tissues. It is unique among glycosaminoglycans in that it is nonsulfated, forms in the plasma membrane instead of the Golgi apparatus, and can be very large, with its molecular weight often reaching the millions.

Heparan sulfate: Heparan sulfate (HS) is a linear polysaccharide found in all animal tissues. It occurs as a proteoglycan (HSPG) in which two or three HS chains are attached in close proximity to cell surface or extracellular matrix proteins.

Dermatan sulfate: Dermatan sulfate is a glycosaminoglycan (formerly called a mucopolysaccharide) found mostly in skin, but also in blood vessels, heart valves, tendons, and lungs. It is also referred to as chondroitin sulfate B, [1] although it is no longer classified as a form of chondroitin sulfate by most sources. The formula is $C_{14}H_{21}NO_{15}S$.

Keratan sulfate: Keratan sulfate (KS), also called keratosulfate, is any of several sulfated glycosaminoglycans (structural carbohydrates) that have been found especially in the cornea, cartilage, and bone. It is also synthesized in the central nervous system where it participates both in development and in the glial scar formation following an injury. Keratan sulfates are large, highly hydrated molecules which in joints can act as a cushion to absorb mechanical shock.

Proteoglycans

Proteoglycans (PGs) are proteins that are heavily glycosylated. The basic proteoglycan unit consists of a "core protein" with one or more covalently attached glycosaminoglycan (GAG) chain(s). Examples of proteoglycans forming part of the present invention are:

Syndecans: Syndecans are single transmembrane domain proteoglycans that are thought to act as co-receptors, especially for G protein-coupled receptors. These core proteins carry heparan sulfate (HS) and chondroitin sulfate (CS) chains. The syndecan protein family has four members; Syndecan 1-4.

Glypicans: Glypicans (GPC) constitute one of the two major families of heparan sulfate proteoglycans, with the other major family being syndecans. Six glypicans have been identified in mammals, and are referred to as GPC1-GPC6.

Biglycan: Biglycan is a small leucine-rich repeat proteoglycan (SLRP) which is found in a variety of extracellular matrix tissues.

Perlecan: Perlecan is a large multidomain (five domains, labeled I-V) proteoglycan that binds to and cross-links many extracellular matrix (ECM) components and cell-surface molecules. Perlecan is synthesized by both vascular endothelial and smooth muscle cells and deposited in the extracellular matrix.

Mimecan;

Decorin;

Versican: Versican is a large extracellular matrix chondroitin sulfate proteoglycan.

Reference Level

In the context of the present invention, the term "reference level" relates to a standard in relation to a quantity, which other values or characteristics can be compared to.

In one embodiment of the present invention, it is possible to determine a reference level by investigating the abundance of one or more of the biomarkers according to the invention in (blood) samples from healthy subjects. By applying different statistical means, such as multivariate analysis, one or more reference levels can be calculated.

Based on these results, a cut-off may be obtained that shows the relationship between the level(s) detected and patients at risk. The cut-off can thereby be used to determine the amount of the one or more biomarkers, which corresponds to for instance an increased risk of multiple sclerosis.

Risk Assessment

The present inventors have successfully developed a new method to predict the risk for developing multiple sclerosis (MS) for a subject. The results presented in the examples show that the described biomarkers (alone or in combination) appear to be efficient biomarkers for determining whether a patient has an increased risk of developing multiple sclerosis.

To determine whether a patient has an increased risk of developing multiple sclerosis a cut-off must be established. This cut-off may be established by the laboratory, the physician or on a case-by-case basis for each patient.

The cut-off level could be established using a number of methods, including: multivariate statistical tests (such as partial least squares discriminant analysis (PLS-DA), random forest, support vector machine, etc.), percentiles, mean plus or minus standard deviation(s); median value; fold changes.

The multivariate discriminant analysis and other risk assessments can be performed on the free or commercially available computer statistical packages (SAS, SPSS, Matlab, R, etc.) or other statistical software packages or screening software known to those skilled in the art.

As obvious to one skilled in the art, in any of the embodiments discussed above, changing the risk cut-off level could change the results of the discriminant analysis for each subject.

Statistics enables evaluation of the significance of each level. Commonly used statistical tests applied to a data set include t-test, f-test or even more advanced tests and methods of comparing data. Using such a test or method enables the determination of whether two or more samples are significantly different or not.

The significance may be determined by the standard statistical methodology known by the person skilled in the art.

The chosen reference level may be changed depending on the mammal/subject for which the test is applied.

Preferably, the subject according to the invention is a human subject, such as a subject considered at risk of having or developing MS.

The chosen reference level may be changed if desired to give a different specificity or sensitivity as known in the art. Sensitivity and specificity are widely used statistics to describe and quantify how good and reliable a biomarker or a diagnostic test is. Sensitivity evaluates how good a biomarker or a diagnostic test is at detecting a disease, while specificity estimates how likely an individual (i.e. control, patient without disease) can be correctly identified as not sick. Several terms are used along with the description of sensitivity and specificity: true positives (TP), true negatives (TN), false negatives (FN) and false positives (FP). If a disease is proven to be present in a sick patient, the result of the diagnostic test is considered to be TP. If a disease is not present in an individual (i.e. control, patient without disease), and the diagnostic test confirms the absence of disease, the test result is TN. If the diagnostic test indicates the presence of disease in an individual with no such disease, the test result is FP. Finally, if the diagnostic test indicates no presence of disease in a patient with disease, the test result is FN.

Sensitivity $$\text{Sensitivity} = TP/(TP+FN) = \text{number of true positive assessments/number of all samples from patients with disease.}$$

As used herein, the sensitivity refers to the measures of the proportion of actual positives, which are correctly identified as such—in analogy with a diagnostic test, i.e. the percentage of people having $PaO_2$ below normal who are identified as having $PaO_2$ below normal.

Specificity $$\text{Specificity} = TN/(TN+FP) = \text{number of true negative assessments/number of all samples from controls.}$$

As used herein, the specificity refers to measures of the proportion of negatives, which are correctly identified. The relationship between both sensitivity and specificity can be assessed by the ROC curve. This graphical representation helps to decide the optimal model through determining the best threshold—or cut-off for a diagnostic test or a biomarker candidate.

As will be generally understood by those skilled in the art, methods for screening are processes of decision-making and therefore the chosen specificity and sensitivity depend on what is considered to be the optimal outcome by a given institution/clinical personnel.

It would be obvious for a person skilled in the art that it may be advantageous to select a higher sensitivity at the expense of lower specificity in most cases, to identify as many patients with disease risk as possible.

In a preferred embodiment, the invention relates to a method with a high specificity, such as at least 70%, such as at least 80%, such as at least 90%, such as at least 95%, such as 100%.

In another preferred embodiment, the invention relates to a method with a high sensitivity, such as at least 80%, such as at least 90%, such as 100%.

Determining Risk of Having or Developing Multiple Sclerosis

In an aspect the invention relates to a method for determining the risk of having or developing multiple sclerosis, in a subject, the method comprising
providing a (previously obtained) biological sample from a subject;
determining the level of at least one biomarker selected from the group consisting of GLX-related glycosaminoglycans (GAGs) and GLX-related proteoglycans (PGs) in said biological sample;
comparing said levels of one or more biomarkers to one or more corresponding reference levels; and
determining that said subject is at risk of developing and/or having multiple sclerosis, if said level of one or more biomarkers are above the one or more reference levels, or determining that said subject is not at risk of developing or having multiple sclerosis, if said one or more levels are equal to or below the one or more reference levels.

As shown in the example section, in both rodent models (example 1) and human MS samples (example 2), GLX-related glycosaminoglycans (GAGs) and GLX-related proteoglycans (PGs) have been identified as biomarkers for risk of having or developing multiple sclerosis.

Thus, in an embodiment, said glycosaminoglycans (GAGs) and proteoglycans (PGs) are GLX related molecules.

In yet an embodiment, the GLX molecules are at least partly brain associated, such as from the cerebrovasculature and/or inflammatory foci and/or the brain proper.

In yet another embodiment, the glycosaminoglycan (GAG) is selected from the group consisting of chondroitin sulfate (CS), hyaluronic acid (HA) and heparan sulfate (HS), dermatan sulfate (DS) or keratin sulfate (KS), preferably chondroitin sulfate (CS). As can be seen in example 2, chondroitin sulfate (CS) shows a strong predictive value.

In another preferred embodiment, the proteoglycan (PG) is selected from the group consisting of Syndecans, Glypicans, Perlecan, Mimecan, Decorin, Versican and Biglycan.

In a more preferred embodiment, the syndecan is selected from the group consisting of Syndecan-4, Syndecan-1, Syndecan-3 and Syndecan-2, preferably syndecan-4. As can be seen in example 2, Syndecan-4 shows a strong predictive value.

In yet a preferred embodiment, the Glypican is selected from the group consisting of Glypican-1, Glypican-2, Glypican-3, Glypican-4, Glypican-5, and Glypican-6, preferably Glypican-1. As can be seen in example 2, glypican-1 shows a strong predictive value.

In an embodiment, the proteoglycan (PG) is Biglycan.

In another embodiment, the risk of having or developing multiple sclerosis is determined in a patient sample at an early stage. Heparan sulfate (HS) levels are shown to be significantly above healthy controls in MOG-injected mice from an early time-point (day 5 in FIG. 2D). Furthermore, chondroitin sulfate (CS) levels are shown to increase significantly (at day 11 in FIG. 2C). In contrast, desease onset in these experimental mice was only after day 13 (see FIG. 2A). Control CS an HS levels were relatively stable throughout the experiment. This difference in time suggests that serum GLX-molecules including CS and HS may represent an early stage biomarker for attack or severity.

The predictive value of the method may be improved if more than one biomarker is determined. Thus, in an embodiment, the level of at least two biomarkers, such as at least three biomarkers are determined. In yet another embodiment, at least the level of chondroitin sulfate (CS) or Syndecan-4 is determined in said biological sample, preferably the level of chondroitin sulfate (CS). As shown in example 2, chondroitin sulfate (CS) and Syndecan-4 provide strong predictive values.

In another embodiment, the level of at least two biomarkers, such as at least three biomarkers, such as at least five biomarkers, such as at least ten biomarkers, such as 14 biomarkers are determined simultaneously. Such a simultaneous determination increases the predictive value of the method while reducing the effort and cost required to obtain the desired information. In addition, when obtaining information relating to several desired biomarkers simultaneously, cross-biomarker sample variability is eliminated, thus improving the data quality.

As outlined in details above, different reference levels may be used. In an embodiment, the reference level is an average level of the one or more individual biomarkers from one or more healthy subjects.

In another embodiment, the method is for determining the risk of having multiple sclerosis. As shown in example 2, the listed biomarkers are all present at higher levels in subjects suffering from MS, compared to healthy control subjects.

The sample type may vary. Thus, in an embodiment, the sample is a blood sample, such as whole blood, serum and/or plasma, preferably plasma or serum. In another embodiment, the biological sample is Cerebrospinal fluid. Preliminary data indicates that Cerebrospinal fluid can also be used as a source for the biological sample.

The levels of the biomarkers may be determined in the sample by different methods. Thus, in yet another embodiment, said level of biomarkers are determined by a method selected from the group consisting of mass spectrometry (GC-MS, LC-MS), HPLC, Raman, NIR, NMR spectroscopy, antibody recognition (e.g. ELISA), Multiplex, dot blotting, and single-molecule array technology. By using a multiplex immunoassay multiple analytes may be measure simultaneously from a single sample and in a single experiment. The skilled person will know how to setup a multiplex assay. Briefly, e.g. microspheres of designated colours are coated with antibodies that are specific to the biomarkers to be quantified. The beads are quantifiable an qualitatively distinguishable by flow cytometry according to their signal intensity and fluorescent signature. The number of biomarkers measured determines the number of bead colours required.

In a preferred embodiment, said subject is a human.

In an embodiment, the method further comprising subgrouping/staging the disease and/or assisting in a prognosis for said subject. As also outlined above, examples of subtypes are isolated syndrome (CIS), Relapsing-remitting MS (RRMS), Primary progressive MS (PPMS) and Secondary progressive MS (SPMS). In yet a preferred embodiment the least one biomarker is selected from the group consisting of
  chondroitin sulfate (CS);
  heparan sulfate (HS);
  hyaluronic acid (HA);
  keratan sulfate (KS);
  dermatan sulfate (DS);
  syndecans, such as Syndecan-4, Syndecan-1, Syndecan-3 and Syndecan-2, preferably syndecan-4;
  Glypicans, such as Glypican-1, Glypican-2, Glypican-3, Glypican-4, Glypican-5, and Glypican-6, preferably Glypican-1;
  Versican;
  Mimecan;
  Decorin;
  Perlacan; and
  Biglycan.

Method for Evaluating the Efficacy of a Treatment Protocol for Prevention, Delay and/or Alleviation of Multiple Sclerosis The biomarkers identified may also find use in methods for evaluating the efficacy of a treatment protocol against multiple sclerosis. Thus, an aspect of the invention relates to a method for evaluating the efficacy of a treatment protocol for prevention, treatment, delay and/or alleviation of multiple sclerosis, the method comprising
  completing the method (for determining the risk of having or developing multiple sclerosis) according to the invention; and for a subject considered at risk of having or developing multiple sclerosis, evaluating whether a treatment protocol for the prevention, treatment, delay or alleviation of multiple sclerosis, results in that said subject is not developing multiple sclerosis, is treated for multiple sclerosis, has delayed disease progression or is alleviated.

Thus, the method may assist in differentiating subjects who are responders from non-responders to a certain treatment regime. Thus, subjects who are not responding to a treatment with many side effects can be removed from such treatment.

Method for Monitoring Disease Progression or Regression of Multiple Sclerosis in a Subject In yet another aspect, the invention relates to a method for monitoring disease progression or regression of multiple sclerosis in a subject, the method comprising
- providing a (previously obtained) first biological sample from a subject considered as having multiple sclerosis or at risk of developing multiple sclerosis;
- determining the level of at least one biomarker selected from the group consisting of GLX-related glycosaminoglycans (GAGs) and GLX-related proteoglycans (PGs), in said first biological sample;
- providing a (previously obtained) second biological sample from the subject, wherein said second sample has been obtained at a later time point than said first sample from said subject;
- determining the level of at least one biomarker selected from the group consisting of GLX-related glycosaminoglycans (GAGs) and GLX-related proteoglycans (PGs), in said second biological sample;
- comparing said levels of one or more biomarkers in said second sample to said one or more corresponding levels in the first sample; and
- determining that
  - said subject has a regression of the multiple sclerosis, if said level of one or more biomarkers in the second sample are lower than the levels in said first sample, or
  - determining that said subject has a progression of the multiple sclerosis, if said level of one or more biomarkers in the second sample are higher than the levels in said first sample, or
  - determining that said subject has no regression or progression of the multiple sclerosis, if said level of one or more biomarkers in the second sample are equal to the levels in said first sample.

In an embodiment, a treatment protocol against MS has been completed or initiated between the sampling of the first and second sample. By comparing samples obtained at different time points it is thus possible to see whether a treatment protocol has an effect. For the present case equals levels in the samples is considered to indicate that the treatment is working in the sense that the disease is not progressing any further. Examples of different treatment regimes for MS are provided elsewhere in this disclosure.

In yet a preferred embodiment the least one biomarker is selected from the group consisting of
- chondroitin sulfate (CS);
- heparan sulfate (HS);
- hyaluronic acid (HA);
- keratan sulfate (KS);
- dermatan sulfate (DS);
- syndecans, such as Syndecan-4, Syndecan-1, Syndecan-3 and Syndecan-2, preferably syndecan-4;
- Glypicans, such as Glypican-1, Glypican-2, Glypican-3, Glypican-4,
- Glypican-5, and Glypican-6, preferably Glypican-1;
- Versican;
- Mimecan;
- Decorin;
- Perlacan; and
- Biglycan.

Method for Evaluating the Efficacy of Treatment to Prevent, Treat, Delay or Alleviate Multiple Sclerosis in a Subject In yet an aspect, the invention relates to a method for evaluating the efficacy of treatment to prevent, treat, delay or alleviate multiple sclerosis in a subject, the method comprising
- providing a (previously obtained) first biological sample from a subject;
- determining the level of at least one biomarker selected from the group consisting of GLX-related glycosaminoglycans (GAGs) and GLX-related proteoglycans (PGs);
- providing a (previously obtained) second biological sample from the subject, wherein said second sample has been obtained at a later time point than said first sample from said subject, and wherein a treatment regime against MS has been initiated or completed between the sampling of the first sample and sampling of the second sample;
- determining the level of at least one biomarker selected from the group consisting of GLX-related glycosaminoglycans (GAGs) and GLX-related proteoglycans (PGs), in said second biological sample;
- comparing said levels of one or more biomarkers in said second sample to said one or more corresponding levels in the first sample; and
- determining that said treatment protocol is working against MS in said subject, if said level of one or more biomarkers in the second sample are lower than or equal to the levels in said first sample, or determining that said treatment protocol is NOT working against MS in said subject if said level of one or more biomarkers in the second sample are higher than the levels in said first sample.

Again, by comparing samples obtained at different time points it is thus possible to see whether a treatment protocol has an effect. For the present case equals levels in the samples is considered to indicate that the treatment is working in the sense that the disease is not progressing any further. Thus, the method may assist in differentiating subjects who are responders from non-responders to a certain treatment regime. Thus, subjects who are not responding to a treatment with many side effects can be removed from such treatment.

Examples of different treatment regimes for MS are provided elsewhere in this disclosure.

In yet a preferred embodiment the least one biomarker is selected from the group consisting of
- chondroitin sulfate (CS);
- heparan sulfate (HS);
- hyaluronic acid (HA);
- keratan sulfate (KS);
- dermatan sulfate (DS);

syndecans, such as Syndecan-4, Syndecan-1, Syndecan-3 and Syndecan-2, preferably syndecan-4;

Glypicans, such as Glypican-1, Glypican-2, Glypican-3, Glypican-4, Glypican-5, and Glypican-6, preferably Glypican-1;

Versican;

Mimecan;

Decorin;

Perlacan; and

Biglycan.

Initiating Treatment Protocol

The method according to the invention may also be used as a tool to evaluate whether a subject should initiate a treatment against MS. Thus, in yet an aspect, the invention relates to a method according to the invention further comprising, for a subject considered at risk of having or developing multiple sclerosis, providing to said subject a treatment protocol for the treatment, prevention, delay and/or alleviation of multiple sclerosis;

and/or;

having said subject under observation for the development of multiple sclerosis.

In an embodiment, the treatment protocol for treatment, prevention, delay and/or alleviation of multiple sclerosis is selected from the group consisting of ozanimod, laquinimod, PEGylated version of interferon-β-1a, PEGylated version of interferon-β-1a, alemtuzumab, daclizumab, CD20 monoclonal antibodies such as rituximab, ocrelizumab and ofatumumab, stem cell therapy, immune modulation, interferon beta-1b, glatirameracetate, mitoxantrone, natalizumab, fingolimod, teriflunomide, dimethyl fumarate, alemtuzumab, daclizumab, ocrelizumab. glucagon-like peptide-1, and metformin. The skilled person would know of other treatment protocols.

In another embodiment, the treatment protocol for treatment, prevention, delay and/or alleviation of multiple sclerosis is selected from the group consisting a dietary regime, a fecal transplantation regime, probiotics, and bone marrow transplantation.

Kit of Parts

The invention also relates to kits of parts. Thus, an aspect of the invention relates to a kit comprising binding agents for at least two biomarkers selected from the group consisting of GLX-related glycosaminoglycans (GAGs) and GLX-related proteoglycans (PGs); and optionally, instructions for using said binding agent in the evaluation of multiple sclerosis in a subject.

In an embodiment, the kit further comprises one or more other binding agents for MS biomarkers, such as a binding agent for TNF-alpha.

In an embodiment, the kit is for use in an ex vivo (or in vivo) method for determining for a subject, the risk of having of multiple sclerosis, the risk of developing of multiple sclerosis and/or the stage of multiple sclerosis.

In another aspect, the invention relates to use of the kit according to the invention in an ex vivo method for determining for a subject the risk of having of multiple sclerosis, the risk of developing of multiple sclerosis and/or the stage of multiple sclerosis.

In a further aspect, the invention relates to the use of one or more binding agents for GLX-related glycosaminoglycans (GAGs) and/or GLX-related proteoglycans (PGs) in an ex vivo (or in vivo) method for determining for a subject the risk of having of multiple sclerosis, the risk of developing of multiple sclerosis and/or the stage of multiple sclerosis.

In yet a further aspect, the invention relates to binding agents for GLX-related glycosaminoglycans (GAGs) and/or GLX-related proteoglycans (PGs) for use in an in vitro method for determining for a subject the risk of having of multiple sclerosis, the risk of developing of multiple sclerosis and/or the stage of multiple sclerosis.

In yet an embodiment relating to the different aspects of the invention, the binding agents are antibodies.

In yet an embodiment, the binding agents, preferably antibodies, are selected from the group consisting of binding agents against chondroitin sulfate (CS);

heparan sulfate (HS);

hyaluronic acid (HA);

keratan sulfate (KS);

dermatan sulfate (DS);

syndecans, such as Syndecan-4, Syndecan-1, Syndecan-3 and Syndecan-2, preferably syndecan-4;

Glypicans, such as Glypican-1, Glypican-2, Glypican-3, Glypican-4, Glypican-5, and Glypican-6, preferably Glypican-1;

Versican;

Mimecan;

Decorin;

Perlacan; and

Biglycan.

It should be noted that embodiments and features described in the context of one of the aspects of the present invention also apply to the other aspects of the invention. Especially it is to be understood that the GLX-related glycosaminoglycans (GAGs) and GLX-related proteoglycans (PGs) listed for one aspect of the invention also applies to the other aspect of the invention.

All patent and non-patent references cited in the present application, are hereby incorporated by reference in their entirety.

The invention will now be described in further details in the following non-limiting examples.

EXAMPLES

Example 1

Aim

To identify glycocalyx (GLX) biomarkers in rat and mice

Materials and Methods

Animals

Female C57Bl/6 mice (Taconic, Denmark (DK) aged 17 weeks (22.8±0.4 g) and female Lewis rats (Charles River, Germany) aged weighing (219±1 g) were housed under standard conditions. Studies were conducted to minimize suffering and were approved by the Danish Animal Inspectorate (2015-15-0201-00647 and 2012-DY-2934-00001). Weight was monitored daily throughout the experiment.

EAE Induction

MOG-induced EAE in C57BL6 mice: EAE was induced in C57Bl/6 mice by active immunization with MOG 35-55 using the kit EK-2110 from Hooke labs (Massachusetts, USA), following the manufacturer's protocol. Briefly, mice were injected subcutaneously (s.c.) at the two flanks with 200 μg of MOG 35-55 emulsified in Complete Freund's adjuvant (CFA; N=9), or 100 µl of PBS in case of the control mice (N=6). At 2 h and 24 h post-immunization the mice were injected i.p. with 100 µl of 4 µg/mL pertussis toxin (PTX) or 100 µl PBS for the control mice. Mice were monitored daily for clinical signs of disease and assigned a disease score according to the EAE clinical scoring system devised by the Danish Animal Experiments Inspectorate (see below).

MBP-Induced EAE in Lewis Rats:

An emulsion consisting of: 100 µL complete Freund's adjuvant (CFA; BD 263810, Denmark (DK)), 200 µg *Mycobacterium tuberculosis* H37Ra (MT; BD, 231141, DK), 100 µg guinea pig myelin basic protein (MBP; Sigma-Aldrich, DK, M2295), and 100 µL 0.9% saline, were prepared.

Directly after preparing, a total of 200 ul emulsion was administered intra-dermally to animals for EAE under isoflurane anesthesia at three sites at the base of the tail, totaling two hundred microliters in volume (N=10). Rats were treated with a small volume of saline twice-daily (100 ul) in accordance with the design of another study. Control rats were treated with 100 ul saline in accordance with the design of another study (N=8).

Clinical Scoring

Clinical scoring was performed blinded twice-daily using the following scale relating to progressive degrees of paralysis: 0, No clinical signs of EAE; 1, Abolished tail tone; 2, Mild paresis of one or both hind legs; 3, Moderate paresis of one or both hind legs; 4, Severe paresis of one or both hind legs; 5, Paresis of one of both hind legs and incipient paresis of one or both forelegs; 6, Moribund. Animals were deemed terminally ill according to predefined humane endpoints designed in consultation with the Danish Animal Inspectorate: animals registering a clinical score of ≥4, or a ≥20% loss of initial body weight.

Timeline Sampling (MOG-EAE)

Before induction and from day 3 post-induction of EAE-MOG, a small volume of blood was collected into EDTA-powdered tubes every second day for dot blot analyses from the facial vein. Blood was spun at 4° C. and plasma isolated, flash frozen in liquid nitrogen and stored at −80° C. for analyses.

At the termination of the experiment (defined as 'peak EAE scoring'), whole blood was isolated under 2% isoflurane anesthesia from the orbital plexus (C57Bl/6; anticoagulant, EDTA) or transcardially (Lewis Rat; anticoagulant; Citrate), spun at 4° C., and plasma isolated, flash frozen in liquid nitrogen and stored at −80° C. for analyses.

Enzyme-Linked Immunosorbent Assay (ELISA)

Hyaluronic acid (HA) in plasma was quantified with a commercially available ELISA kit (Echelon Biosciences, K-1200, Roskilde, DK).

Plasma Dot Blotting

Due to the small volumes of plasma available with serial sampling, dot blots were used to assess GLX markers longitudinally. Two µl of plasma was dotted in duplicate on a cationic nitrocellulose membrane (Hybond N+, Amersham, GE Healthcare, Brondby, Denmark) and allowed to dry. The membrane was incubated for 60 minutes at room temperature in blocking buffer: 5% skim milk powder (Sigma-Aldrich) in tris-buffered saline+0.05% Tween20 (TBS-T; Sigma-Aldrich). The membrane was incubated thereafter with primary antibodies at their respective dilutions overnight, at 4° C. Membranes were thereafter washed in TBS-T and incubated with secondary antibodies conjugated to horseradish peroxidase, diluted at respective dilutions in blocking buffer, and raised against the source of the primary for 60 mins. Membranes were washed thoroughly with TBS-T and finally, in TBS. Membranes were visualized with Supersignal West femto luminescent substrate and Chemidoc XRS CCD camera (Bio-Rad Laboratories). Chemiluminescence was quantified with densitometry after normalizing to background with ImageJ software. Membranes were thereafter stripped with Restore Stripping Buffer (ThermoScientific, 21509) for 10 minutes at room temperature, washed in TBS and complete stripping confirmed with identical development protocol (Femto, CCD camera). Membranes were blocked again with blocking buffer and probed for different antigens of interest (Second probe).

Primary antibodies: First probing: Heparan sulfate (HS) (1:1000, 10E4, cat no H1890, US Biological, MA, USA), Syndecan-1 (1:750, 281-1, cat no 553712, BD Pharmingen, Brøndby, Denmark), Syndecan-4 (1:750, KY8/2, cat no 550350, BD Pharmingen). Second probing: Chondroitin sulfate (CS) (1:1000, CS-56, cat no C8035, Sigma-Aldrich, Brødnby, Denmark), Syndecan-3 (1:1000, cat no AF3539, R&D Systems, UK). HA (cat no 5029-9990, Bio-Rad, USA), glypican-1 (cat no AF4519, R&D Systems), Biglycan (cat no ab 109369, Abcam, UK), dermatan sulfate (cat no D3208, USBiologics), keratan sulfate (cat no K0197, USBiologics) Secondary: HRP-conjugated: anti-rabbit (1:2000), anti-rat (1:4000), anti-mouse (1:3000) (DAKO, Glostrup, DK).

Data Analysis:

Data sets were tested for normality (Shapiro-Wilk) and equal variance before statistical analyses were performed. Weight and dot blot data (MOG-EAE) were assessed with Two-Way ANOVA or Student's t-test (MBP-EAE), ELISA data was assessed with Student's T-test and clinical scoring (MOG-EAE) was tested with Wilcoxon signed-rank test to determine when the median clinical score was statistically above 0. A P-value of <0.05 was reported as statistically significantly different. Data are presented as mean±S.E.M for normal data and median ±interquartile range for non-normal data. Longitudinal data from MOG-EAE is presented as normalized to Day −1, before the EAE emulsion was administered.

Results

EAE Induction

All animals receiving EAE emulsions developed a clinical score and experienced weight loss throughout the experiment representing a penetrance of 100% (FIG. 1A, FIG. 2A). Weight loss coincided with clinical presentation in both MOG-EAE and in late-stage (clinical score 4) MBP-EAE. In MOG-EAE, clinical scoring was significantly above 0 from day 14 until termination (Day 20) with a peak, median clinical score of 2.5 (Day 19), and weight loss significantly different from healthy controls from day 13.

Detection of Glycocalyx Shedding in Plasma: Glycosaminoglycans

In MOG-injected mice, heparan sulfate (HS) levels were significantly above healthy controls from an early timepoint, day 5, and remained significantly above until day 11 (FIG. 2D), and thereafter remained not significantly above controls.

In contrast, Chondroitin sulfate (CS) levels were detected at similar levels to controls until day 11 where CS increased significantly (FIG. 2C). This difference progressed steadily until the termination of the experiment where CS levels in MOG-EAE mice were ~2-fold above controls. Control CS levels were relatively stable throughout the experiment.

Due to the volume required for ELISA, hyaluronic acid (HA) was only detected at termination of the experiment. As shown in FIG. 2B, MOG-EAE resulted in significantly increased concentrations in plasma relative to controls (~2.5-fold from 86.8±9.8 ng/mL to 236.6±25.7 ng/mL).

In late-stage MBP-EAE in Lewis rats, similar results were obtained for each GAG: HS levels were not different from controls (FIG. 1D), whereas CS and HA levels were ~1.5-fold significantly above control levels (FIG. 2B,C).

Detection of Glycocalyx Shedding in Plasma: Proteoglycans

Syndecan-1, 3, and 4 were detected in plasma of MOG-EAE and respective controls over the course of EAE induction and progression (FIG. 3). All three markers were relatively stable throughout the MOG-EAE disease course, albeit inclusive of day-to-day fluctuation (FIG. 2E). Syndecan-1 in MOG-EAE was significantly above controls at day 13, however it was not significantly different at the termination of the experiment.

In late-stage MBP-EAE, a similar pattern was observed: no differences were detected between MBP-EAE and controls for Syn-1, Syn-4 (FIG. 1E, F) respectively, albeit a trend was detected in favour of higher shedding of Syn-4 in late-stage MBP-EAE (FIG. 1F, p=0.07).

Conclusion

In both MOG-EAE and MBP-EAE, GLX markers chondroitin sulfate (CS) and 35 hyaluronic acid (HA) were significantly increased in the plasma of diseased animals compared to healthy controls. Additionally, at late-stage of both MOG-EAE and MBP-EAE, all diseased animals were above the highest levels of control animals (i.e. no overlap in signal), with the exception of one EAE rat for CS. This is highly relevant for the applicability as a biomarker. This suggests that the biomarkers may be able to, with very high reproducibility, distinguish between diseased patients and healthy individuals without overlap of signal.

Interestingly, these distinct glycan molecules would not be detected in proteomic screens of plasma and therefore may represent a new class of candidate biomarkers.

To further validate the results from rodents further analysis was conducted in blood from human MS patients.

Example 2

Blood and CSF from Human MS Patients

Aim

To validate the rodent results relating to experimental MS, and test five human patient samples for presence and absence of GLX markers, the relation of these markers to disease and non-disease, and assess the variation of these markers in five patients over a longitudinal time scale. Furthermore, in the following experiments, utilizing the same methodology for detection of GLX markers as in example 1, we assessed GLX markers in blood for additional classes of GLX components to expand the breadth of the findings in rodents. These GLX marker data were then plotted with MRI scan data to search for correlation between markers and brain lesions. Moreover, in a second experiment, nineteen MS patients and 20 healthy controls were included to test for BiGlycan in the serum with the method described. Finally, cerebrospinal fluid (CSF) from 9 MS patients were tested for syndecan-3 with the method described.

Materials and Methods

Blood samples were acquired through phlebotomy and CSF through spinal puncture.

As described above, 2 ul of sample is dotted, in duplicate, and probed for detection with antibodies specific for the markers described in FIG. 3. Visualisation and optical density analysis is performed as above with a secondary antibody-HRP complex and chemiluminescence (femtogram resolution). Test were performed for the following biomarkers:
Proteoglycans:
Syndecan-1
Syndecan-3
Syndecan-4
Glypican-1,
CD44
BiGlycan
Glycosaminoglycans:
Chondroitin Sulfates (CS)
Hyaluronic Acids (HA)
Heparan Sulfates (HS)
Keratan Sulfates
Dermatan Sulfates
MRI Acquisition and Analysis Frequent high-resolution 3T MRI consisting of a baseline MRI followed by seven consecutive weekly MRI exams was performed on five RRMS patients with no disease-modifying treatment. MRI acquisitions were performed on a 3T MRI system and only 3D FLAIR and 3D-T1-Gd images were analyzed. Normalized signal intensities were measured on subtraction images comparing a given time-point to the first time-point in that patient.

Results

Figure 5:
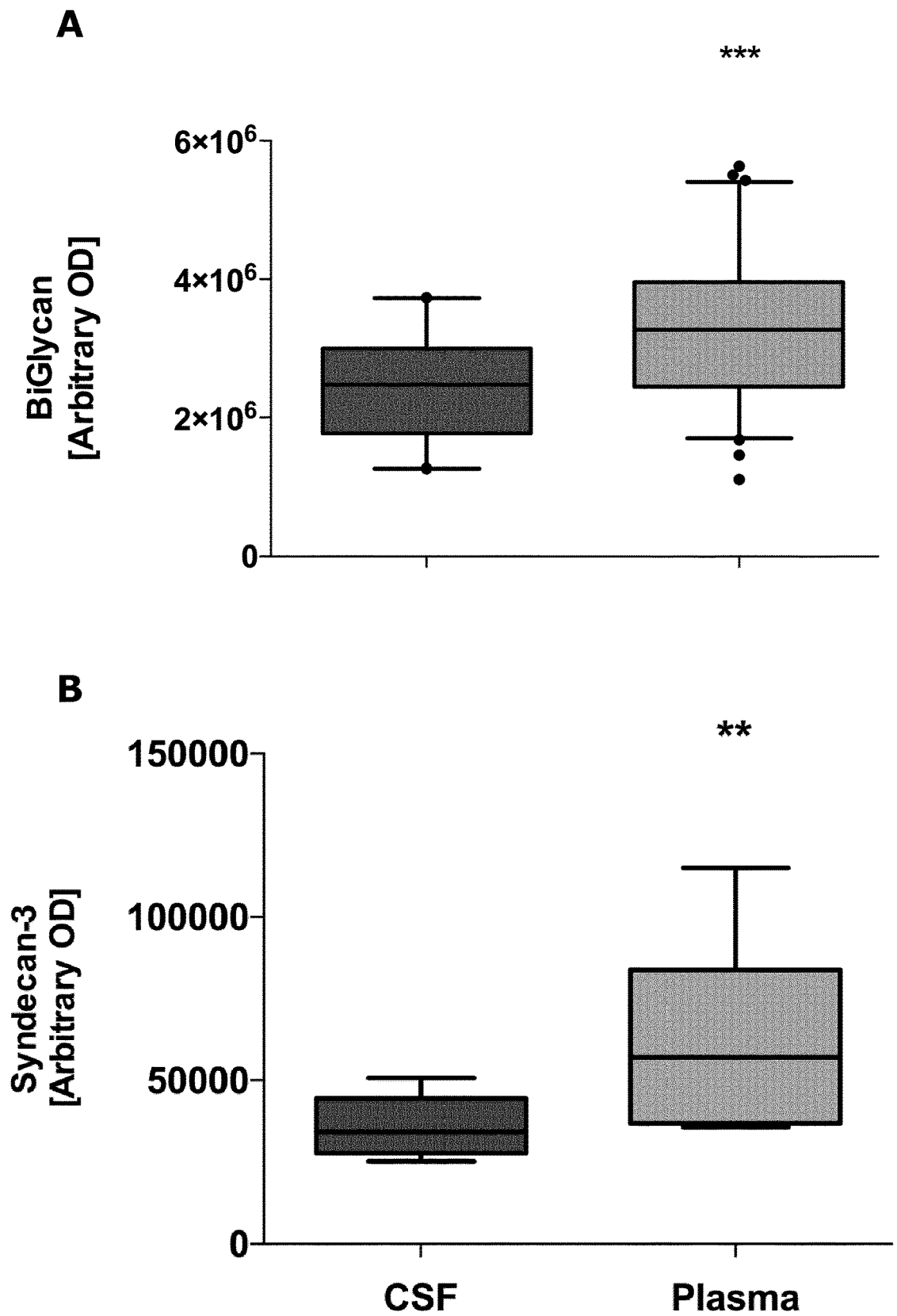

As seen in FIG. 3 and FIG. 5, all GLX markers are detectable above background in all patient and healthy control samples. All GLX markers display a unique signature both between patients and healthy controls and within each patient over the timescale. As seen in FIG. 3, Chondroitin Sulfate (CS) and Syndecan-4 are particularly effective in separating healthy control samples from MS patient sample, regardless of patient or time point and BiGlycan also shows low overlap between healthy and MS sample. Syndecan-3 is detectable in CSF of MS patients albeit to a lesser extent than plasma. Preliminary data also indicates than keratan sulfate and dermatan sulfate may also be a relevant biomarkers (data not shown).

Conclusion

In this set of experiments, it is shown that GLX components across different classes, are elevated and variable between MS patients and over time within each patient and thus should be considered as potential biomarkers of disease, disease severity, and treatment response. The classes of GLX that have shown to be of substantial relevance are glycosaminoglycans (GAGs) and proteoglycans (PGs).

Within these groups, the following classes have been investigated: PGs: Syndecans, Glypicans, BiGlycans; GAGs: Chondroitin Sulfates, Hyaluronic Acids, Heparan Sulfates, Keratan Sulfates (detectable, not shown), Dermatan Sulfates (detectable, not shown).

When taken together with the rodent models we have provided evidence for GLX components consisting of: PGs: Syndecans, Glypicans, BiGlycans; GAGs: Chondroitin Sulfates, Hyaluronic Acids, Heparan Sulfates, Keratan Sulfates, Dermatan Sulfates. These represent the vast majority of the GLX structure and are all responsive to MS disease.

The invention claimed is:

1. A method for monitoring disease progression or regression of multiple sclerosis (MS) in a subject, the method comprising:
    detecting the level of at least two biomarkers in a first biological sample from a subject considered as having multiple sclerosis or at risk of developing multiple sclerosis, whereby at least one biomarker is selected from GLX-related glycosaminoglycans (GAGs), and at least one biomarker is selected from GLX-related proteoglycans (PGs);
    detecting the level of the same at least two biomarkers in a second biological sample from the subject, wherein said second biological sample has been obtained at a different time point than said first biological sample from said subject;
    comparing the levels of the at least two biomarkers detected in the second biological sample;
    determining a cut-off level using a multivariate statistical analysis comprising machine learning, wherein the machine learning transforms the levels of the at least two biomarkers detected in the first and/or second samples to the cut-off level; and
    determining that the subject has a progression or a regression of MS if the levels of the at least two biomarkers detected in the first biological sample differ from the levels of the at least two biomarkers detected in the second biological sample with respect to the cut-off level,
    wherein the cut-off level indicates the progression or regression of MS, and
    wherein the at least two biomarkers in the first biological sample and the same at least two biomarkers in the second biological sample are detected by a method selected from the group consisting of: binding agents, immunoassays, antibody recognition, multiplexing, dot blotting, beads, microspheres, single-molecule array technology, mass spectrometry, HPLC, Raman spectroscopy, NIR spectroscopy, and NMR spectroscopy.

2. The method according to claim 1, wherein the at least one biomarker of GLX-related glycosaminoglycans (GAGs) comprises at least one biomarker selected from keratan sulfate (KS), chondroitin sulfate (CS), hyaluronic acid (HA), heparan sulfate (HS), or dermatan sulfate.

3. The method according to claim 1, wherein the at least one biomarker of GLX-related proteoglycans (PGs) comprises at least one biomarker selected from CD44, Syndecans, Glypicans, Biglycan, Perlecan, Mimecan, Decorin, or Versican.

4. The method according to claim 3, wherein the Syndecans are selected from the group consisting of Syndecan-4, Syndecan-1, Syndecan-3 and Syndecan-2.

5. The method according to claim 3, wherein the Glypicans are selected from the group consisting of Glypican-1, Glypican-2, Glypican-3, Glypican-4, Glypican-5, and Glypican-6.

6. The method according to claim 1, wherein the at least one biomarker of GLX-related proteoglycans (PGs) comprises CD44 or Perlecan.

7. The method according to claim 1, wherein the at least one biomarker of GLX-related glycosaminoglycans (GAGs) comprises HA.

8. The method according claim 1, wherein the at least one biomarker of GLX-related glycosaminoglycans (GAGs) comprises HA and the at least one biomarker of GLX-related proteoglycans (PGs) comprises CD44 or Perlecan.

9. The method according to claim 1, wherein the first and second biological samples comprise whole blood, serum, plasma, or cerebrospinal fluid.

10. The method according to claim 1, further comprising subgrouping or staging the disease, or providing a prognosis for said subject.

11. The method according to claim 1, where the subject is a human subject.

12. The method according to claim 1, further comprising administering or inducing one to administer to said subject a treatment for MS when said subject is determined to have a progression of the multiple sclerosis or when said subject is determined to have no regression or progression of the multiple sclerosis.

13. The method according to claim 1, further comprising administering or inducing one to administer to said subject a CD20 monoclonal antibody, a stem cell therapy, or an immune modulator when said subject is determined to have a progression of the multiple sclerosis or when said subject is determined to have no regression or progression of the multiple sclerosis.

14. The method according to claim 1, further comprising administering or inducing one to administer to said subject a dietary regime, a fecal transplantation regime, probiotics, or bone marrow transplantation when said subject is determined to have a progression of the multiple sclerosis or when said subject is determined to have no regression or progression of the multiple sclerosis.

15. The method according to claim 1, further comprising administering or inducing one to administer to said subject ozanimod, laquinimod, a PEGylated version of interferon-β-1a, alemtuzumab, daclizumab, rituximab, ocrelizumab, ofatumumab, interferon βB-1b, glatirameracetate, mitoxantrone, natalizumab, fingolimod, teriflunomide, dimethyl fumarate, glucagon-like peptide-1, or metformin when said subject is determined to have a progression of the multiple sclerosis or when said subject is determined to have no regression or progression of the multiple sclerosis.

16. The method according to claim 1, further comprising administering to said subject magnetic resonance imaging (MRI).

17. The method according to claim 16, wherein the MRI comprises a gadolinium-enhancement sequence.

18. The method according to claim 16, wherein the MRI comprises a fluid attenuation inversion recovery (FLAIR) sequence.

19. The method according to claim 17, wherein the MRI further comprises a fluid attenuation inversion recovery (FLAIR) sequence.

20. The method according to claim 1, wherein the multivariate statistical analyses comprises a partial least squares discriminate analysis.

21. The method according to claim 1, wherein the multivariate statistical analyses comprises a random forest analysis.

22. The method according to claim 1, wherein the multivariate statistical analyses comprises a support vector machine.

23. The method according to claim 1, wherein the different time point of obtaining the second biological sample is a later time point than said first biological sample from said subject.

24. The method according to claim 1, wherein the different time point of obtaining the second biological sample is a prior time point than said first biological sample from said subject.

25. A method for monitoring disease risk, progression, or regression of multiple sclerosis (MS) in a subject, the method comprising:
- detecting the level of at least two biomarkers in a first biological sample from a subject considered as having multiple sclerosis or at risk of developing multiple sclerosis, whereby at least one biomarker is selected from GLX-related glycosaminoglycans (GAGs), and at least one biomarker is selected from GLX-related proteoglycans (PGs);
- comparing the levels of the at least two biomarkers in the first biological sample to reference levels for the at least two biomarkers;
- determining a cut-off level using a multivariate statistical analysis comprising machine learning, which transforms the levels of the at least two biomarkers detected in the first biological sample to the cut-off level; and
- determining that the subject has a progression or a regression of MS if the levels of the at least two biomarkers detected in the first biological sample differ from the reference levels for the at least two biomarkers with respect to the cut-off level,
- wherein the cut-off level indicates a risk of MS or the progression or regression of MS, and
- wherein the at least two biomarkers in the first biological sample are detected by a method selected from the group consisting of: binding agents, immunoassays, antibody recognition, multiplexing, dot blotting, beads, microspheres, single-molecule array technology, mass spectrometry, HPLC, Raman spectroscopy, NIR spectroscopy, and NMR spectroscopy.

26. A method for monitoring disease progression or regression of multiple sclerosis (MS) in a subject, the method comprising:
- detecting the level of at least two biomarkers in a first biological sample from a subject considered as having multiple sclerosis or at risk of developing multiple sclerosis, whereby at least one of the biomarkers is selected from GLX-related glycosaminoglycans (GAGs);
- detecting the level of the same at least two biomarkers in a second biological sample from the subject, wherein said second biological sample has been obtained at a different time point than said first biological sample from said subject;
- comparing the levels of the at least two biomarkers detected in the second biological sample;
- determining a cut-off level using a multivariate statistical analysis comprising machine learning, wherein the machine learning transforms the levels of the at least two biomarkers detected in the first and/or second samples to the cut-off level; and
- determining that the subject has a progression or a regression of MS if the levels of the at least two biomarkers detected in the first biological sample differ from the levels of the at least two biomarkers detected in the second biological sample with respect to the cut-off level,
- wherein the cut-off level indicates the progression or regression of MS, and
- wherein the at least two biomarkers in the first biological sample and the same at least two biomarkers in the second biological sample are detected by a method selected from the group consisting of: binding agents, immunoassays, antibody recognition, multiplexing, dot blotting, beads, microspheres, single-molecule array technology, mass spectrometry, HPLC, Raman spectroscopy, NIR spectroscopy, and NMR spectroscopy.

27. A method for monitoring disease progression or regression of multiple sclerosis (MS) in a subject, the method comprising:
- detecting the level of at least two biomarkers in a first biological sample from a subject considered as having multiple sclerosis or at risk of developing multiple sclerosis, whereby at least one of the biomarkers is selected from GLX-related proteoglycans (PGs);
- detecting the level of the same at least two biomarkers in a second biological sample from the subject, wherein said second biological sample has been obtained at a different time point than said first biological sample from said subject;
- comparing the levels of the at least two biomarkers detected in the second biological sample;
- determining a cut-off level using a multivariate statistical analysis comprising machine learning, wherein the machine learning transforms the levels of the at least two biomarkers detected in the first and/or second samples to the cut-off level; and
- determining that the subject has a progression or a regression of MS if the levels of the at least two biomarkers detected in the first biological sample differ from the levels of the at least two biomarkers detected in the second biological sample with respect to the cut-off level,
- wherein the cut-off level indicates the progression or regression of MS, and
- wherein the at least two biomarkers in the first biological sample and the same at least two biomarkers in the second biological sample are detected by a method selected from the group consisting of: binding agents, immunoassays, antibody recognition, multiplexing, dot blotting, beads, microspheres, single-molecule array technology, mass spectrometry, HPLC, Raman spectroscopy, NIR spectroscopy, and NMR spectroscopy.

28. A method for monitoring disease risk, progression, or regression of multiple sclerosis (MS) in a subject, the method comprising:
- detecting the level of at least two biomarkers in a first biological sample from a subject considered as having multiple sclerosis or at risk of developing multiple sclerosis, whereby at least one of the biomarkers is selected from GLX-related glycosaminoglycans (GAGs);
- comparing the levels of the at least two biomarkers in the first biological sample to reference levels for the at least two biomarkers;
- determining a cut-off level using a multivariate statistical analysis comprising machine learning, which transforms the levels of the at least two biomarkers detected in the first biological sample to the cut-off level; and
- determining that the subject has a progression or a regression of MS if the levels of the at least two biomarkers detected in the first biological sample differ from the reference levels for the at least two biomarkers with respect to the cut-off level,
- wherein the cut-off level indicates a risk of MS or the progression or regression of MS, and
- wherein the at least two biomarkers in the first biological sample are detected by a method selected from the group consisting of: binding agents, immunoassays, antibody recognition, multiplexing, dot blotting, beads, microspheres, single-molecule array technology, mass spectrometry, HPLC, Raman spectroscopy, NIR spectroscopy, and NMR spectroscopy.

29. A method for monitoring disease risk, progression, or regression of multiple sclerosis (MS) in a subject, the method comprising:

detecting the level of at least two biomarkers in a first biological sample from a subject considered as having multiple sclerosis or at risk of developing multiple sclerosis, whereby at least one of the biomarkers is selected from GLX-related proteoglycans (PGs);

comparing the levels of the at least two biomarkers in the first biological sample to reference levels for the at least two biomarkers;

determining a cut-off level using a multivariate statistical analysis comprising machine learning, which transforms the levels of the at least two biomarkers detected in the first biological sample to the cut-off level; and determining that the subject has a progression or a regression of MS if the levels of the at least two biomarkers detected in the first biological sample differ from the reference levels for the at least two biomarkers with respect to the cut-off level, wherein the cut-off level indicates a risk of MS or the progression or regression of MS, and wherein the at least two biomarkers in the first biological sample are detected by a method selected from the group consisting of: binding agents, immunoassays, antibody recognition, multiplexing, dot blotting, beads, microspheres, single-molecule array technology, mass spectrometry, HPLC, Raman spectroscopy, NIR spectroscopy, and NMR spectroscopy.

* * * * *